United States Patent
Bian et al.

(10) Patent No.: US 10,240,190 B2
(45) Date of Patent: Mar. 26, 2019

(54) NANO-CONSTRUCTS FOR POLYNUCLEOTIDE DELIVERY

(71) Applicant: THE CHINESE UNIVERSITY OF HONG KONG, Shatin, N.T., Hong Kong (CN)

(72) Inventors: Liming Bian, Hong Kong (CN); Chung Hang Jonathan Choi, Hong Kong (CN); Chun Kit Choi, Hong Kong (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 20 days.

(21) Appl. No.: 15/010,801

(22) Filed: Jan. 29, 2016

(65) Prior Publication Data

US 2016/0220708 A1 Aug. 4, 2016

Related U.S. Application Data

(60) Provisional application No. 62/110,916, filed on Feb. 2, 2015.

(51) Int. Cl.
| | |
|---|---|
| C08G 73/02 | (2006.01) |
| C08K 3/10 | (2018.01) |
| C08F 283/00 | (2006.01) |
| C12Q 1/6834 | (2018.01) |
| C12Q 1/6841 | (2018.01) |
| A61K 49/00 | (2006.01) |
| C12N 15/87 | (2006.01) |
| A61K 47/69 | (2017.01) |
| B82Y 5/00 | (2011.01) |
| C12N 15/11 | (2006.01) |

(52) U.S. Cl.
CPC ........ *C12Q 1/6834* (2013.01); *A61K 47/6923* (2017.08); *A61K 47/6929* (2017.08); *A61K 49/0065* (2013.01); *C12N 15/87* (2013.01); *C12Q 1/6841* (2013.01); *B82Y 5/00* (2013.01); *C12N 15/111* (2013.01); *C12N 2310/141* (2013.01); *C12N 2320/10* (2013.01); *C12N 2320/32* (2013.01)

(58) Field of Classification Search
CPC ............ C12Q 1/6841; C12Q 2525/207; C12Q 2525/301; C12Q 2563/155; C12Q 1/6834; A61K 47/48861; A61K 47/48884; A61K 49/0065; B82Y 5/00; C12N 15/111; C12N 15/87; C12N 2310/141; C12N 2320/10; C12N 2320/32

See application file for complete search history.

(56) References Cited

U.S. PATENT DOCUMENTS

2009/0322327 A1* 12/2009 Gao .................. B82Y 5/00
    324/307
2014/0105828 A1* 4/2014 Yang ................ A61K 47/48884
    424/9.323

OTHER PUBLICATIONS

Rana et al 2012, Advanced Drug Delivery Rev. 64:200-216.*
Lin et al 2014, ACS Nano 8:3876-3883.*
Li et al 2014, Analytical Chemistry 86:10148-10156.*
Heuer-Jungemann et al 2013 Nanoscale 5:9503-9510.*
Dubertret et al., Single-mismatch detection using gold-quenched fluorescent oligonucleotides nature biotechnology 2001 pp. 365-370.*
Black et al Polydopamine-enabled surface functionalization of gold nanorods for cancer cell-targeted imaging and photothermal therapy Nanomedicine (Lond). Jan. 2013; 8(1): 17-28.*
Lee et al., Mussel-Inspired Surface Chemistry for Multifunctional Coatings 2007 Science pp. 426-430.*
Lytton-Jean et al, Five Years of si RNA Delivery: Spotlight on Gold Nanoparticles Small 2011, 7, No. 14, 1932-1937.*
Koo Lee et al., Effective Gene Silencing by Multilayered siRNA-Coated Gold Nanoparticles small 2011, 7, No. 3, 364-370.*

* cited by examiner

*Primary Examiner* — Maria G Leavitt
(74) *Attorney, Agent, or Firm* — Kilpatrick Townsend & Stockton LLP

(57) ABSTRACT

The present invention provides novel nano-constructs useful for delivering polynucleotides into cells, methods of using the nano-constructs, and methods of making the nano-constructs.

12 Claims, 18 Drawing Sheets

Specification includes a Sequence Listing.

SEQUENCE LISTING

```
<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: synthetic nucleotide sequence hsa-miR-29b

<400> SEQUENCE: 1
uagcaccauu ugaaaucagu guu                                           23

<210> SEQ ID NO 2
<211> LENGTH: 21
<212> TYPE: DNA
<213> ORGANISM: Artificial Sequence
<220> FEATURE:
<223> OTHER INFORMATION: synthetic nucleotide sequence hsa-miR-31

<400> SEQUENCE: 2
aggcaagaug cuggcauagc u                                             21

<210> SEQ ID NO 3
<211> LENGTH: 23
<212> TYPE: DNA
<213> ORGANISM: Artificial Sequence
<220> FEATURE:
<223> OTHER INFORMATION: synthetic nucleotide sequence - DNA analog of
      hsa-miR-29b

<400> SEQUENCE: 3
tagcaccatt tgaaatcagt gtt                                           23

<210> SEQ ID NO 4
<211> LENGTH: 35
<212> TYPE: DNA
<213> ORGANISM: Artificial Sequence
<220> FEATURE:
<223> OTHER INFORMATION: synthetic nucleotide sequence - FITC-labeled
      hpDNA-29b
<220> FEATURE:
<221> NAME/KEY: misc_feature
<222> LOCATION: (1)..(1)
<223> OTHER INFORMATION: 5' end labeled with fluorescein isothiocyanate
      (FITC)

<400> SEQUENCE: 4
ccgggtaaca ctgatttcaa atggtgctaa cccgg                              35

<210> SEQ ID NO 5
<211> LENGTH: 33
<212> TYPE: DNA
<213> ORGANISM: Artificial Sequence
<220> FEATURE:
<223> OTHER INFORMATION: synthetic nucleotide sequence - Cy3-labeled
      hpDNA-31
<220> FEATURE:
```

-continued

```
<221> NAME/KEY: misc_feature
<222> LOCATION: (1)..(1)
<223> OTHER INFORMATION: 5' end labeled with cyanine 3 (Cy3)

<400> SEQUENCE: 5
ccgggtagct atgccagcat cttgcctacc cgg                                33

<210> SEQ ID NO 6
<211> LENGTH: 22
<212> TYPE: DNA
<213> ORGANISM: Artificial Sequence
<220> FEATURE:
<223> OTHER INFORMATION: synthetic nucleotide sequence - scrambled FITC
      labeled DNA
<220> FEATURE:
<221> NAME/KEY: misc_feature
<222> LOCATION: (1)..(1)
<223> OTHER INFORMATION: 5' end labeled with fluorescein isothiocyanate
      (FITC)

<400> SEQUENCE: 6
gctgctttat agagcctgtt ga                                            22

<210> SEQ ID NO 7
<211> LENGTH: 22
<212> TYPE: DNA
<213> ORGANISM: Artificial Sequence
<220> FEATURE:
<223> OTHER INFORMATION: synthetic nucleotide sequence - random DNA

<400> SEQUENCE: 7
cagtggtttt accctatggt ag                                            22
```

NANO-CONSTRUCTS FOR POLYNUCLEOTIDE DELIVERY

RELATED APPLICATIONS

This application claims priority to U.S. Provisional Patent Application No. 62/110,916, filed Feb. 2, 2015, the contents of which are hereby incorporated by reference in the entirety for all purposes.

BACKGROUND OF THE INVENTION

MicroRNAs (miRNAs) are single-stranded non-coding small RNA molecules, typically in the length range of 21-23 nucleotides. Found in plants and animals, these short RNAs are important regulators of gene expression by way of silencing of specific target mRNAs and/or suppressing translation of specific target mRNAs. Well conserved across a broad spectrum of plant and animal species, miRNAs are believed to be a vital and evolutionarily ancient component of genetic regulation mechanism.

Since miRNAs were first recognized as a distinct class of biological regulators in the early 2000s, much effort has been devoted to miRNA research. It has been revealed that different sets of miRNAs are expressed in different cell types and tissues and that miRNAs play multiple roles during plant and animal development as well as in a variety of other biological processes. Furthermore, aberrant expression of miRNAs has been implicated in numerous disease states, including different types of cancer. Given the biological importance of miRNAs, there exists an urgent need for new and more effective means of miRNA delivery in various therapeutic applications as well as for useful research tools in the ongoing miRNA studies. This invention fulfills this and other related needs.

BRIEF SUMMARY OF THE INVENTION

This invention provides new methods and compositions useful for introducing a polynucleotide into cells, which can serve as effective means for cell transfection or for detecting polynucleotides of interest within live cells (e.g., certain miRNAs). In one aspect, the present invention provides a novel nanoparticle-based construct comprising (1) a core particle having a diameter of 1-1000 nm; (2) a polymer coating on the surface of the core particle having a thickness of 1-100 nm; and (3) a polynucleotide non-covalently attached to the polymer coating.

In some embodiments, the polynucleotide of the nano-construct comprises a core segment, a first pairing segment located at the 5' of the core segment, and a second pairing segment located at the 3' of the core segment, wherein the polynucleotide is further attached to a detectable label, wherein: when the core segment is not hybridized to its complementary sequence, the first and second pairing segments hybridize with each other so as to allow the polynucleotide to assume a hair-pin configuration, and when the core segment is hybridized to its complementary sequence, the first and second pairing segment separate from each other so as to allow the polynucleotide to assume an open configuration. The core segment in some cases is 15-30 nucleotide in length and hybridizes to a target miRNA of a predetermined nucleotide sequence. In some cases, each of the pairing segments is 5-10 nucleotides in length.

In some embodiments, the core particle of the nano-contruct comprises a metal, such as gold. The core particle may be 10-100, 30-60, or 40-50 nm in diameter. In some embodiments, the polymer coating comprises polydopamine. The polymer coating may be 1-10 or 4-5 nm in thickness. In some embodiments, the polynucleotide is attached to a detectable label, for example, a fluorescent molecule such as fluorescein isothiocyanate (FITC) or cyanine 3 (Cy3).

In a second aspect, the invention provides a composition comprising the nano-construct of described above and a cell, particularly a live cell, such as a live stem cell. In some embodiments, the composition comprises two or more such nano-constructs, with each of the nanoconstructs comprising a different fluorescent molecule and a different core segment.

In a third aspect, the present invention provides a method for introducing a polynucleotide into a cell by contacting the cell with the nano-construct described above. In some embodiments, the method further comprises the the steps of (1) contacting the nano-construct of this invention with a cell under conditions permissible for the nano-construct to hybridize with an miRNA having a nucleotide sequence complementary to the core segment; and (2) detecting signal from the detectable label, wherein an increase in the signal compared to a control signal indicates the presence of the miRNA. In some cases, step (2) is repeated at a later time and the signal detected at the later time is compared with the signal detected at the first time, wherein an increase or decrease from the signal detected at the first time indicates an increase or decrease, respectively, in the miRNA level. In some embodiments, the cell is a live cell, such as a live stem cell. In some cases, the cell is in the body of a living organism. In some embodiments, the miRNA is miR-29b or miR-31. In some embodiments, the detectable label is a fluorescent molecule, such as fluorescein isothiocyanate (FITC) or cyanine 3 (Cy3).

In a third aspect, the present invention provides a method for making the nano-construct described above. The method comprises the following steps: (1) contacting a core particle with a polymer solution to permit a polymer coating to form on the surface of the core particle, wherein the core particle has a diameter of 1-1000 nm and the coating has a thickness of 1-100 nm; and (2) contacting the coated core particle with a polynucleotide to permit the polynucleotide to become non-covalently attached to the coating. Optionally, the polynucleotide is further attached to a detectable label.

In some embodiments, the polynucleotide comprises a core segment, a first pairing segment located at the 5' of the core segment, and a second pairing segment located at the 3' of the core segment, wherein: when the core segment is not hybridized to its complementary sequence, the first and second pairing segments hybridize with each other so as to allow the polynucleotide to assume a hair-pin configuration, and when the core segment is hybridized to its complementary sequence, the first and second pairing segment separate from each other so as to allow the polynucleotide to assume an open configuration. In some cases, the core segment is 15-30 nucleotide in length and hybridizes to a target miRNA of a predetermined nucleotide sequence. In some cases, each of the pairing segments is 5-10 nucleotides in length.

In some embodiments, the core particle comprises a metal, such as gold. Typically, the core particle is 10-100, 30-60, or 40-50 nm in diameter. In some embodiments, the polymer coating the core particle is polydopamine. Typically, the coating is 1-10 or 4-5 nm in thickness. In some embodiments, the detectable label is attached to the 5' of the polynucleotide. In some embodiments, the detectable label is a fluorescent molecule, such as fluorescein isothiocyanate (FITC) or cyanine 3 (Cy3).

BRIEF DESCRIPTION OF THE DRAWINGS

FIG. 1A shows, Preparation of the polydopamine-coated gold nanoparticles (Au@PDA NPs) and hairpin-DNA-based (hpDNA) nanoprobes. FIG. 1B shows, Intracellular detection of miRNAs in living human mesenchymal stem cells (hMSCs).

FIG. 2A shows UV-vis spectra of aqueous solution of AuNPs and Au@PDA NPs. Inset: Photographs of AuNPs (left) and Au@PDA NPs (right) show the color change after the coating of AuNPs with a thin PDA shell. FIG. 2B shows Representative TEM images of Au@PDA NPs. Inset: Magnified image of a single Au@PDA NP showing clearly its core-shell structure.

FIG. 3B shows Release profile of the nanoprobes for miR-29b detection in buffer. Inset: Plot of percentage of release versus concentration of DNA analog of target miR-29b. Data obtained from 3 independent measurements are presented as mean±SD. FITC: Ex: 480 nm; Em: 520 nm. Cy3: Ex: 520 nm; Em: 565 nm.

FIG. 4A shows Light-scattering images of (i) untreated hMSCs, (ii) AuNPs-treated hMSCs, and (iii) Au@PDA NPs-treated hMSCs. FIG. 4B shows (i) TEM micrographs of hMSCs incubated with Au@PDA NPs for 24 h. (ii) and (iii) are the enlargement of boxed area of (i) and (ii), respectively. Nu=nucleus, Cy=cytosol. FIG. 4C shows ICP-OES measurement of hMSCs treated with Au@PDA NPs and nanoprobes for 24 h. The Au content of cell-associated nanoparticles is determined using a standard curve (FIG. 16) and represented by Au content per well. Data obtained from 3 independent measurements are presented as mean±SD.

FIG. 5A shows Confocal images of hMSCs treated with nanoprobes targeting miR-29b (green). FIG. 5B shows Confocal images of hMSCs treated with nanoprobes targeting miR-31 (red). Results show that hMSCs express detectable levels of miR-29b and miR-31 in a time-dependent manner and only in differentiating status. Scale bar is 100 µm.

FIG. 8A shows AuNPs are coated with a PDA shell of ~10 nm thickness in 0.1 mg/mL of dopamine solution. FIG. 9B shows AuNPs are coated with a PDA shell of ~35 nm thickness in 0.4 mg/mL of dopamine solution. The PDA shell thickness can be easily tuned by simply varying the dopamine concentration while keeping the reaction time constant as 1 h.

FIG. 11A shows Photographs of AuNP@PDA NPs before and after incubation in different solutions for 24 h. The solutions remain clear without obvious aggregation. α-MEM=alpha minimum essential medium, FBS=fetal bovine serum. FIG. 11B shows UV-vis spectra of the solutions shown in FIG. 11A. No significant red-shift of the $\lambda_{max}$ is observed in all the solutions, supporting our observation that no obvious aggregation happens.

DETAILED DESCRIPTION OF THE INVENTION

I. Introduction

Figure 1A:
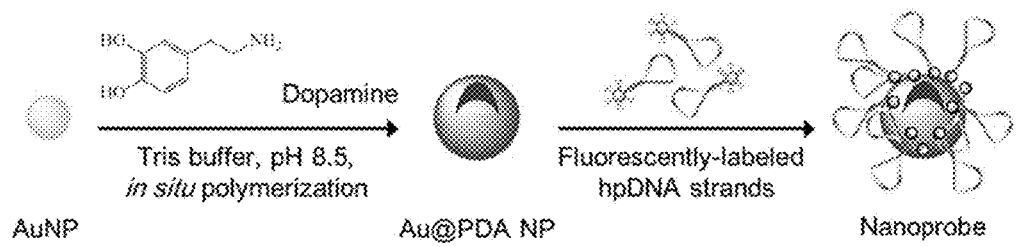
FIGS. 1A-1B.

The capability of delivering polynucleotides into living cells is crucial to the understanding of cell biology, for example, in order to effectively detect miRNAs of interest in live cells, it is important to be able to introduce the appropriate probes for such miRNAs into the cells; yet conventional methods for intracellular detection of miRNAs requires a high cell population as well as cell lysis. The present inventors have created a nanoparticle-based construct, which in some cases may serve as an effective carrier for transferring or delivering polynucleotide molecules into cells, for example, for transfecting cells with polynucleotide sequences encoding mRNA or proteins, or other polynucleotides such as miRNA, siRNA, shRNA, pRNA, and the like. In some other cases, the nano-construct may serve as a nanoprobe for detecting miRNAs inside living cells with high sensitivity and specificity. These nano-constructs can enter the cells naturally without the need for transfection agents. They can be customized to detect different target microRNAs and are also amenable to simultaneous multiplexed detection of multiple target miRNAs in living cells. Using these nano-constructs, one can readily investigate the differentiation status of living stem cells (e.g., differentiated versus undifferentiated). Because of their unique construction of having a polynucleotide non-covalently attached to the polymer coating of the core particle, it is believed that a favorable configuration of the polynucleotide is achieved in comparison with the configuration typically resulted from a covalent conjugation of the polynucleotide at a distinct location to a solid support. This favorable configuration surprisingly increases stability of the polynucleotide, possibly due to the configuration rendering the polynucleotide more resistant to enzymatic cleavage within a cellular environment.

In short, the nano-contructs of this invention are particularly effective for their intended purposes owing to the enhanced stability. As nanoprobes, the nano-constructs of this invention present the distinct advantages of (1) detecting miRNAs in living cells without the need for transfection agents; (2) multiplexed detection of multiple target RNAs in living cells; and (3) tracking of differentiation status of living stem cells.

II. Production of Nano-Constructs

A. General

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

In this disclosure the size of nucleic acids or polynucleotides is given in kilobases (kb), base pairs (bp), or nucleotides (nt). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of any polynucleotide of interest and any synthetic oligonucleotide can be verified after manipulation using well-known sequencing methods, e.g., the chain termination method for sequencing double-stranded templates of Wallace et al., *Gene* 16: 21-26 (1981).

B. Components and Preparation of Nano-Constructs

The nano-construct of this invention comprises these components: (1) a core particle; (2) a polymer coating on the outside of the core particle; (3) a polynucleotide adsorbed to the polymer coating; and optionally (4) a detectable label or moiety attached to the polynucleotide. At the core of each of the nano-constructs of this invention is a particle that may comprise a metal, a natural or synthetic polymer, or an inorganic material. Typically, the core particle is in the size range of about 1-1000 nm in diameter, in some cases about 10-100 nm in diameter. The core particle is first coated with a thin and uniform layer of an appropriate polymer (e.g., polydopamine) before a polynucleotide probe, in some cases already labeled with a detectable molecule, is adsorbed onto the polymer layer.

Suitable metals for the core particles include nearly all types of metals, except for the alkali metals (Group 1 elements) and the alkaline earth metals (Group 2 elements). Transition metals such as Au, Ag, Cu, Fe, Ni, and Zn are useful for this purpose. Suitable polymers for forming the core particles in this invention include naturally occurring or synthetic polymers, so long as the polymers exhibit no detectable cytotoxicity within the concentration range of practical applications. Some examples of the polymers include poly(lactic acid) (PLA), poly(glycolic acid) (PGA), poly(lactic-co-glycolic acid) (PLGA), polycaprolactone (PCL), and polystyrene (PS). Suitable inorganic material for making the core particles is typically a metal oxide or a metalloid oxide, for example, silica, alumina, iron oxide, quantum dots, lanthanide-doped nanoparticles.

Various techniques are known for producing nanoparticles that can serve as the core particles of the nano-contructs of this invention. For example, gold nanoparticles can be produced by a number of methods well-known in the pertinent field. Some commonly used methods involve a liquid environment. The so-called "liquid chemical methods" generate gold nanoparticles by reduction of chloroauric acid (H[AuCl$_4$]). After dissolving H[AuCl$_4$], the solution is rapidly stirred while a reducing agent is added. This causes Au$^i$ ions to be reduced to neutral gold atoms. As more and more of these gold atoms form, the solution becomes supersaturated, and gold gradually starts to precipitate in the form of sub-nanometer particles. The rest of the gold atoms that form stick to the existing particles, and, if the solution is stirred vigorously enough, the particles will be fairly uniform in size. Gold nanoparticles can also be synthesized by laser ablation in liquids, see, e.g., Amendola and Meneghetti, *Phys. Chem. Chem. Phys.*, 2009, 11, 3805-3821. For the purpose of the present invention, the gold nanoparticles are typically within the diameter range of 1-1000 nm, for example, in the range of about 10-100, 20-80, 30-60, or 40-50 nm, and often in the range of about 40-45 nm.

The second component of the nanoprobe of this invention is a polymer coating on the outer surface of the core particle. A variety of polymers can be used for coating the gold particle, so long as the polymer exhibits no or little cytotoxicity and is able to bind a polynucleotide non-covalently (e.g., by electrostatic attraction, van der Waals forces, and/or hydrophobic effects) and, preferably, is also able to adequately quench the detectable signal emitted by the detectable label attached to the polynucleotide when the polynucleotide is bound to the polymer. For example, a polymer that is positively charged in general may be useful for its ability to bind the negative charged polynucleotide. In some cases, the monomers, prior to polymerization to form their polymer, are chosen for their ability to quickly self-polymerization. Polydopamine (PDA) is a suitable polymer due to its abundant catechol and amino groups providing positive charge as well as the relative ease in inducing polymerization. For polydopamine and related materials derived from polydopamine, see review of polydopamine and its derivative materials, Liu et al., *Chem. Rev.* 2014, 114(9); 5057-5115. Further examples include: i) norepinephrine/epinephrine; ii) 5,6-dihydroxyindole; iii) poly(l-lysine) (PLL)/alginate, PLL/poly(l-glutamic acid), PLL/poly(methacrylic acid) (PMA), and PLL/cholesterol-modified PMA (PMAc).

The polymer coating on the core particles is usually formed by placing the core particles in a solution of the monomer (prior to formation of their polymer). Depending on the nature of the polymer, concentrations of the monomer as well as the core particles may be adjusted to ensure proper thickness of the coating. For example, the concentration of gold particles may be in the range of about 10-100 µg/ml, or about 20-80, 30-50, 40-50, or just about 40 µg/ml. As another example, the concentration of dopamine prior to polymerization may be in the range of about 0.01-0.2 mg/ml, or about 0.02-0.1, or just about 0.05 mg/ml. Typically, the polymer coating formed on the outside of the core particles in a monomer solution is thin and uniform: thickness in the range of about 1-100 nm, or about 1-10, 2-8, 3-6, 4-5 nm, or just about 4.5 nm. The total diameter of the coated core particles is generally in the range of about 1-1000 nm, more often about 15-220 nm, for example, about 40-60 nm, or just about 50 nm.

The third component of the nano-construct is a polynucleotide, which may be of virtually any nucleotide sequence and practical any length. In the case of a nanoprobe constructed for detecting miRNA, the polynucleotide comprises a core segment and two pairing segments each located on one side of the core segment: the first pairing segment is located at the 5' of the core segment, and a second pairing segment is located at the 3' of the core segment. The core segment has a nucleotide sequence that is generally complement to the pre-determined sequence of a target miRNA, so as to allow hybridization between the core segment and the target miRNA under suitable conditions based on Watson-Crick base-pairing. In most cases, the core segment sequence complements with the target miRNA sequence 100%, while in other cases the percentage complementarity may be just below 100%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, or at least 96%. The core segment is generally in the length range of about 15-25 nucleotides, often in the range of about 21-23 nucleotides. In other words, there could be 1, 2, 3, 4, or up to 5 mis-matched nucleotides between the core segment sequence and the target miRNA.

The two pairing segments straddling the core segment are intended for hybridizing with each other, based on Watson-Crick base-pairing, so as to fold the entire polynucleotide into a hair-pin like configuration, when the core segment is not hybridized with its target miRNA. On the other hand, once the core segment is hybridized with its target miRNA, the two pairing segments become disengaged and the hair-pin configuration becomes open. To achieve this goal, the pairing segments are typically shorter in length than the core segment. For example, each of the pairing segments may be about 5-10 nucleotides in length.

Aside from the core segment and the two pairing segments, the polynucleotide component of the nanoprobe may optionally contain additional nucleotides in its sequence. In general, the overall length of the polynucleotide is in the range of 30-100 nucleotides, often 35-50 nucleotides.

The fourth and, in some cases optional, component of the nano-construct of this invention is the detectable label. As already mentioned in the last section, the detectable label is attached to the polynucleotide, often by a covalent bound at a distinct location of the polynucleotide, for example, at the 5' of the polynucleotide. The detectable label or detectable moiety of the polynucleotide is a molecule that emits a signal that is readily detectable by spectroscopic, photochemical, biochemical, immunochemical, chemical, or other physical means. For example, useful labels include fluorescent dyes, electron-dense reagents, enzymes, radioisotopes. Different types of detectable molecules may be suitable for use in this invention, for example, various fluorophores such as fluorescein isothiocyanate (FITC) and cyanine 3 (Cy3) can be used in this invention. In some cases, the detectable label is a fluorescence emitter, and the fluorescence emitted may be quenched by the polymer coating and the gold particle by virtue of being within close physical proximity. In other cases, the detectable label is a fluorescence emitter, and the fluorescence emitted may be quenched by a quencher molecule, which may be either located on the polymer coating or attached to the polynucleotide at a location that permits effective quenching when the polynucleotide assumes the hair-pin configuration but permits effective emission of a detectable signal upon hybridization between the core segment and its target miRNA. For example, the fluorescent moiety and its quencher may be located at the opposite ends of the polynucleotide.

III. Detection of miRNAs

Aside from the general purpose of delivering a polynucleotide of interest into a cell, the nano-construct of this invention is particularly useful as a nanoprobe designed to detect specific miRNAs. The nanoprobe of the present invention allows rapid detection of the presence and quantity of a target miRNA by detecting the detectable signal (and changes therein) emitted from a detectable moiety located on the probe when the polynucleotide component of the probe become hybridized with the target miRNA. While similar techniques have been in use before, the present inventors made the surprising discovery that their nanoprobes are particularly effective for detecting and monitoring changes in miRNA levels in live cells such as differentiating stem cells, for example, in live human mesenchymal stem cells (hMSCs), permitting researchers to accurately and in real time track events related to differentiation (e.g., osteogenic differentiation) within these cells. This high level of effectiveness in detection and monitoring is achieved at least in part due to the efficient uptake of the nanoprobes by the live stem cells as well as the significantly enhanced stability of the polynucleotide probe within the cells.

This is a completely unexpected finding since previous studies indicate significant difficulties in performing similar detection techniques within live stem cells. Utilizing the miRNA detecting techniques developed from the discovery by the present inventors, one is able to quickly detect multiple miRNAs and monitor their changing levels in live stem cells by way of using multiple nanoprobes bearing distinct detectable labels for distinct specificity for different miRNAs and by way of performing such testing at multiple time points to track activation of different miRNAs during stem cell differentiation process.

EXAMPLES

The following examples are provided by way of illustration only and not by way of limitation. Those of skill in the art will readily recognize a variety of non-critical parameters that could be changed or modified to yield essentially the same or similar results.

The present invention employs a novel polydopamine coating on the nanoparticle. This coating helps quench the fluorescence of the DNA probes bound to the nanoparticle, and thereby enhances signal to noise ratio by reducing the background signal. Therefore, this invention specifically entails live cell detection of miRNAs, which generally exist at low concentration in the cells. MicroRNAs are an emerging class of biomarkers that are linked to many cellular processes, including differentiation. It is shown that stem cell behavior, such as differentiation, can be monitored through intracelllular profiling of specific microRNA markers related to differentiation. This novel coating also allows for attachment of the DNA probes on the particle via the physical bonding, which is more facile than chemical bonding as used in the existing techniques. Furthermore, compared to the end-on attachment of the DNA probes on the nanoparticle in the existing techniques, the side-on attachment of the DNA probes on the polydopamine coating makes the DNA probes less exposed to the degrading activities of intracellular nucleases. This effectively extends the working life span of the nanoprobes inside the cells.

Example 1

The capability to monitor the differentiation process in living stem cells is crucial to the understanding of stem cell biology and practical application of stem-cell therapies, yet conventional methods for the analysis of biomarkers related to differentiation requires a large number of cells as well as cell lysis. Such requirements lead to unavoidable loss of cell sources and preclude real-time monitoring of cellular events. In this disclosure, the inventors report the detection of microRNAs (miRNAs) in living human mesenchymal stem cells (hMSCs) using polydopamine—coated gold nanoparticles (Au@PDA NPs). The PDA shell facilitates the immobilization of fluorescently-labeled hairpin DNA strands (hpDNAs) that can recognize specific miRNA targets. The gold core and PDA shell quenches the fluorescence of the immobilized hpDNAs, and subsequent binding of the hpDNAs to the target miRNAs leads to the dissociation from Au@PDA NPs and recovery of fluorescence signals. Remarkably, these Au@PDA-hpDNA nanoprobes can naturally enter stem cells, which are known for their poor transfection efficiency, without the aid of transfection agents. Upon cellular uptake of these nanoprobes, intense and time-dependent fluorescence responses were observed from two important osteogenic marker miRNAs, miR-29b and miR-31, only in hMSCs undergoing osteogenesis and living primary osteoblasts but not in undifferentiated hMSCs and 3T3 fibroblasts. These results demonstrate the capability of such Au@PDA-hpDNA nanoprobes for monitoring the differentiation status of hMSCs (i.e., differentiating versus undifferentiated) via the detection of specific miRNAs in living stem cells. The modular design of the nanoprobes of this invention enables facile customization and shows great promise in the investigation on the dynamics of stem cell differentiations, identification and isolation of specific cell types, and high-throughput drug screening.

Introduction

Human mesenchymal stem cells (hMSCs) serve as a very promising cell source for tissue engineering and regenerative medicine, owing to their ease of isolation and multipotency to differentiate to various lineages including adipocytes, osteoblasts, and chondrocytes[1]. Determination of the differentiation status of hMSCs (e.g., differentiating versus undifferentiated) is critical to the application of hMSCs in cell-based therapies[2,3]. To achieve this, end-point methods such as real-time polymerase chain reaction (RT-PCR) and western blot are conventionally utilized to confirm the expression of certain differentiation-relevant marker genes[4] or proteins[5]. Although these analytical methods are reliable, a large number of cell samples and lysis of the cells are required for the analysis. Such requirements also lead to unavoidable loss of cell source and preclude real-time monitoring of cellular activities. More recently developed techniques including fluorescence-activated cell sorting[6,7] (FACS) and surface-enhanced Raman spectroscopy[8] (SERS) offer a non-destructive alternative to sort or distinguish differentiated and undifferentiated stem cells via examination of the changes in membranous features in living stem cells. However, these techniques generally require expensive staining reagents or specialized instruments. More importantly, they are not suitable for detecting intracellular biomarkers. In this regard, developing a facile and non-invasive way to either monitor the differentiation process or distinguish the differentiation status of living stem cells is highly desirable. MicroRNAs (miRNAs) are single-stranded non-coding RNAs with a typical short length of 21-23 nucleotides[9]. They play an important role in controlling the expression of target proteins via either repression of the messenger RNAs (mRNAs) or inhibition of mRNA translation in a sequence-specific manner, thereby providing an additional level of gene regulation[10,11]. In particular to stem cell studies, miRNAs have newly emerged as a mediator of various stem cell behaviors, including differentiation[12-15]. Some specific miRNAs are found to be dynamically expressed and their expressions are highly correlated with the stem cell differentiation process[16-19]. miR-29b20 and miR-3121 are two distinct miRNA markers that support the osteogenesis of hMSCs. Profiling studies [18,21,22] show that these specific miRNAs are significantly up-regulated in stem cells following the induction of osteogenic differentiation. The dynamic nature of miRNA expression highlights that miRNAs may function as viable biomarkers for monitoring the differentiation progress of stem cells. While much effort has been devoted to tracking intracellular messenger RNAs (mRNAs)[23-25], only a few attempts have been reported to detect cancer-related miRNAs in cancer cells[26,27]. In addition, these previous efforts mainly focus on cancerous cell lines which are easy to transfect[28]. Prior to the present invention, no one has demonstrated the detection of miRNAs in living stem cells with reasonable transfection efficiency[29].

Figure 1B:
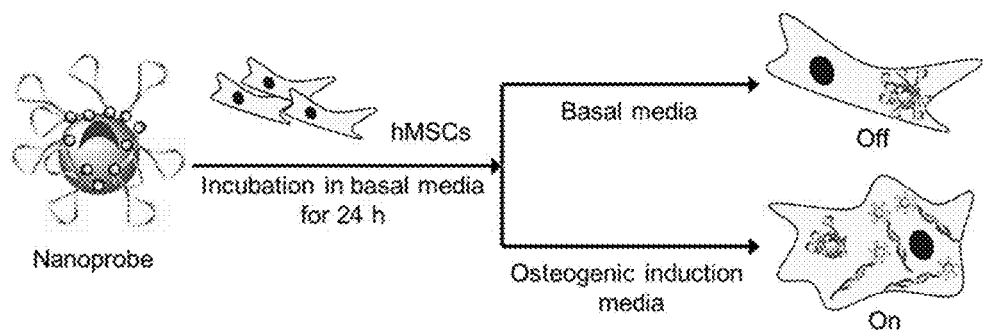

In this study, a novel hairpin-DNA-based nanoprobe is used for detecting specific miRNAs in living hMSCs. This nanoprobe possesses a core-shell structure formed by depositing a layer of polydopamine (PDA) on the surface of a gold nanoparticle (AuNP) core via in situ polymerization under alkaline conditions. Such gold-PDA core-shell nanoparticles (Au@PDA NPs) are amenable to subsequent immobilization of fluorescently-labeled hairpin DNA strands (hpDNAs) on the PDA shell (FIG. 1A). The resultant Au@PDA-hpDNA NPs (termed as "nanoprobes") can naturally enter stem cells without the aid of transfection agents. Due to the close proximity between hpDNAs and the AuNP core (<5 nm)[30] and compounded by the intrinsic quenching properties of PDA shell [25], the immobilized hpDNAs on the nanoprobes do not fluoresce appreciably. In the presence of miRNA target with a sequence complementary to the recognition region of the immobilized hpDNAs, it has been shown in buffer that the specific binding between the hpDNAs and the target miRNAs triggers the dissociation of hpDNAs from Au@PDA NPs, and thereafter generating a detectable fluorescent signal. Using these nanoprobes, the present inventors demonstrate the specific detection of two important osteogenic marker miRNAs, miR-29b and miR-31, in living hMSCs undergoing osteogenic differentiation as well as living osteoblasts (FIG. 1B).

Results and Discussion

Preparation and Characterization of Au@PDA NPs.

Figure 2A:
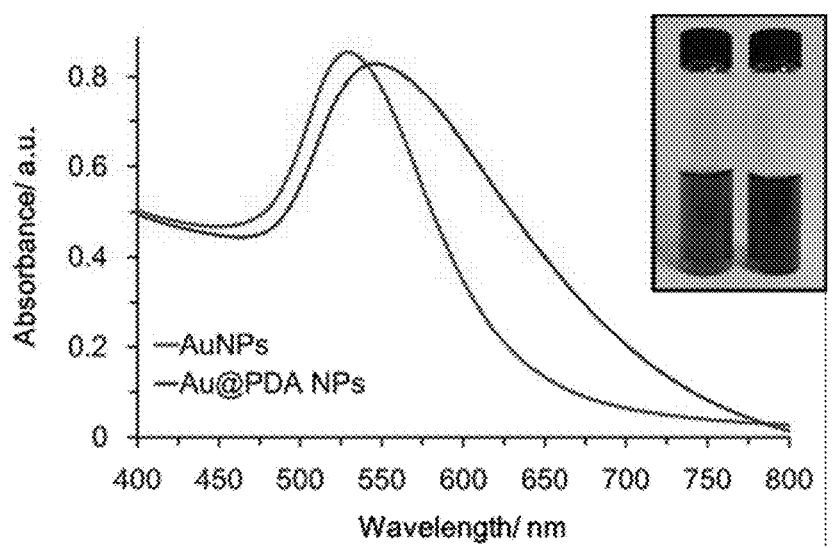
FIGS. 2A-2B Characterization of Au@PDA NPs.
Figure 2B:
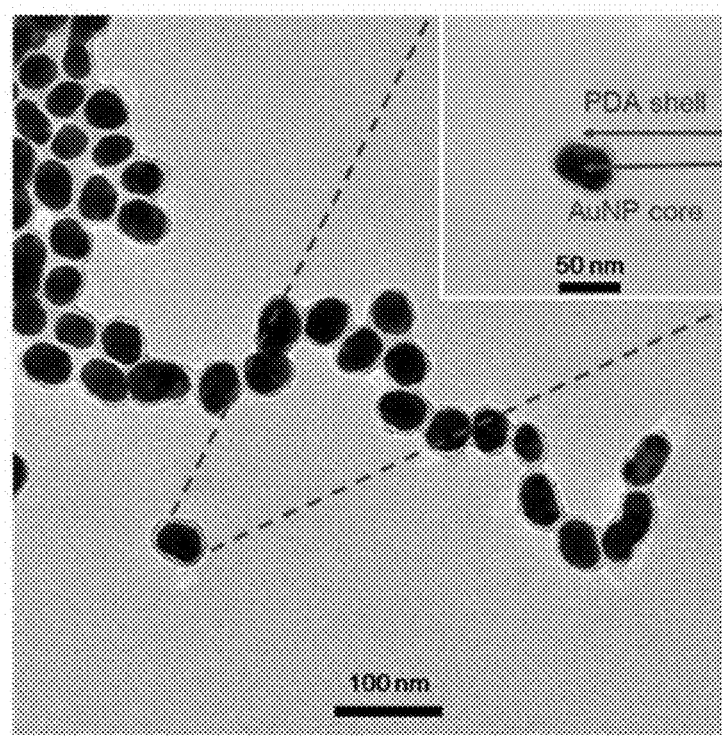
Figure 8A:
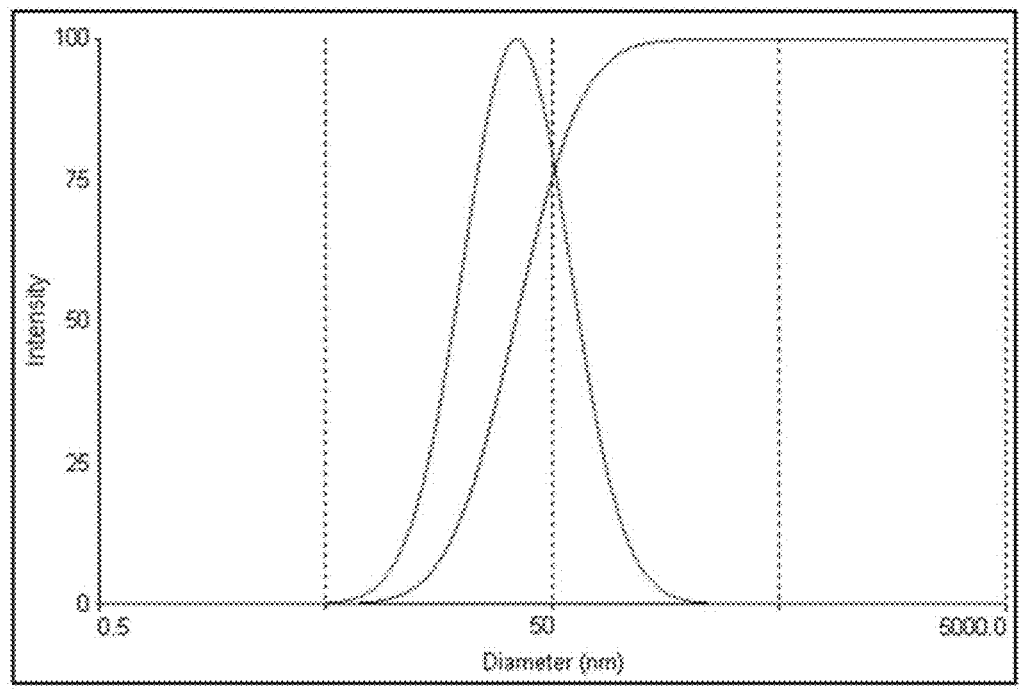
FIGS. 8A-8B Dynamic light scattering (DLS) measurements of FIG. 8A AuNPs and FIG. 8B Au@PDA NPs in water at 25° C. The hydrodynamic size of AuNPs increases by around 12 nm after coating with the thin PDA shell, which is consistent with the TEM measurements.
Figure 8B:
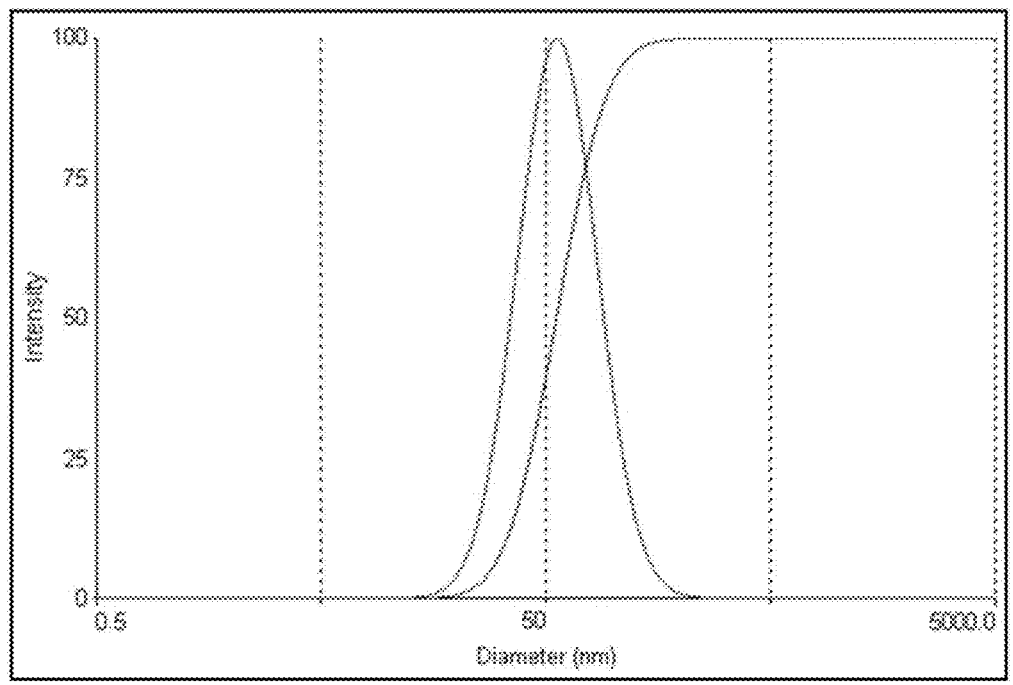
Figure 9A:
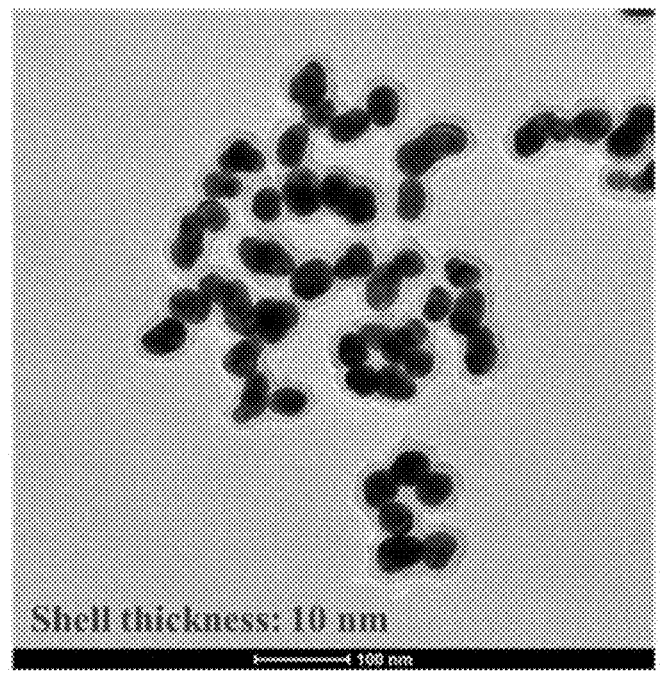
FIGS. 9A-9B Representative TEM images of Au@PDA NPs with different PDA shell thicknesses.
Figure 9B:
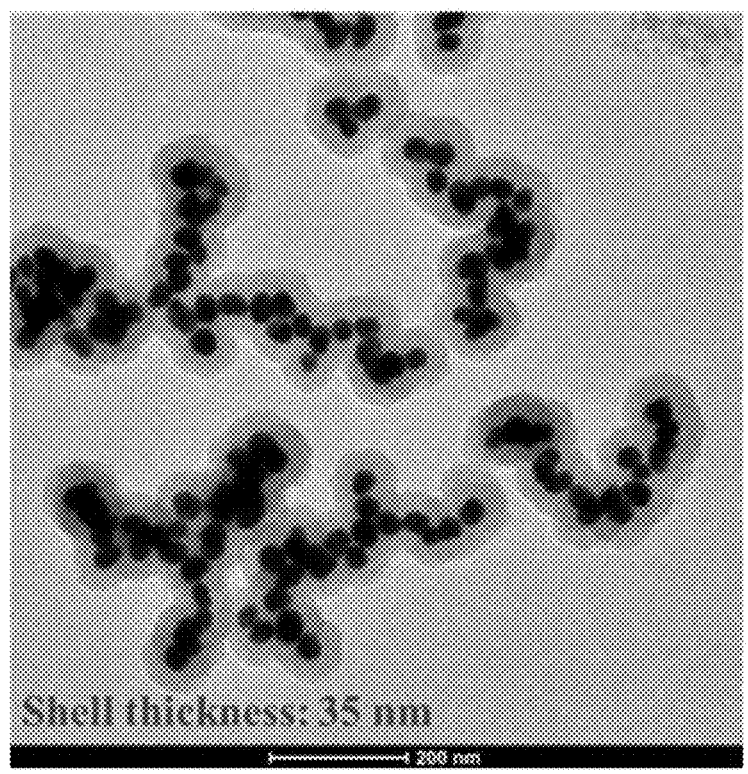
Figure 10:
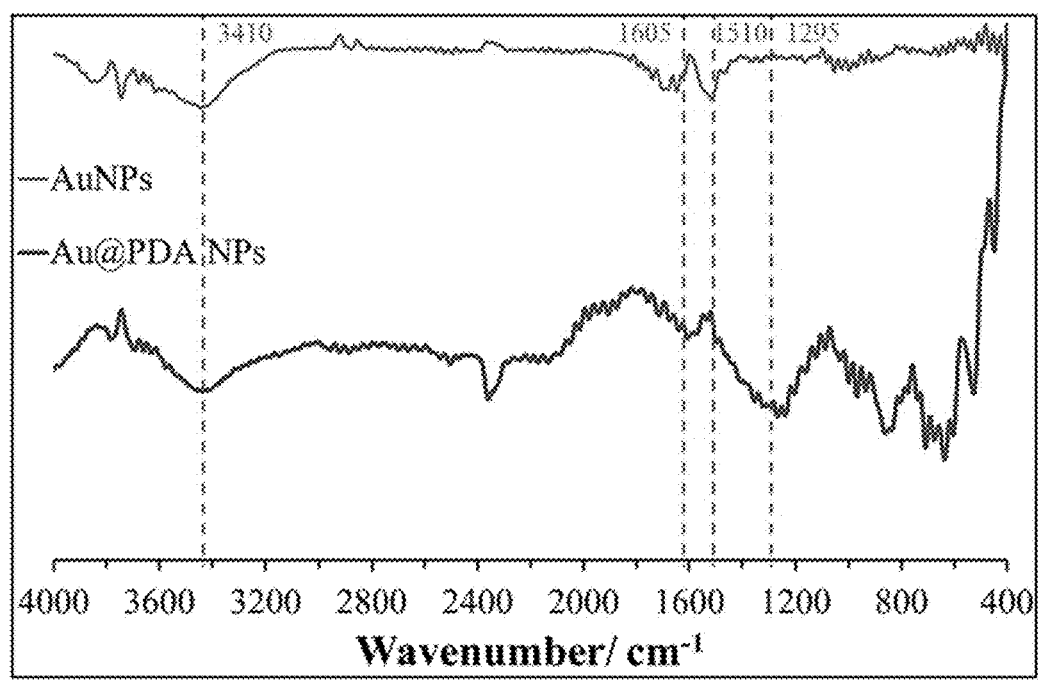
FIG. 10 FT-IR spectra of AuNPs (red) and Au@PDA NPs (purple). Newly emerged absorption bands at 3410 cm$^{-1}$ (stretching vibration of phenolic O—H and N—H), 1605 cm$^{-1}$ (stretching vibration of aromatic ring and bending vibration of N—H), 1510 cm$^{-1}$ (shearing vibration of N—H), and 1295 cm$^{-1}$ (stretching vibration of phenolic C—O) are observed after coating AuNPs with PDA, indicating the presence of the PDA shell on the surface of AuNPs.
Figure 11A:
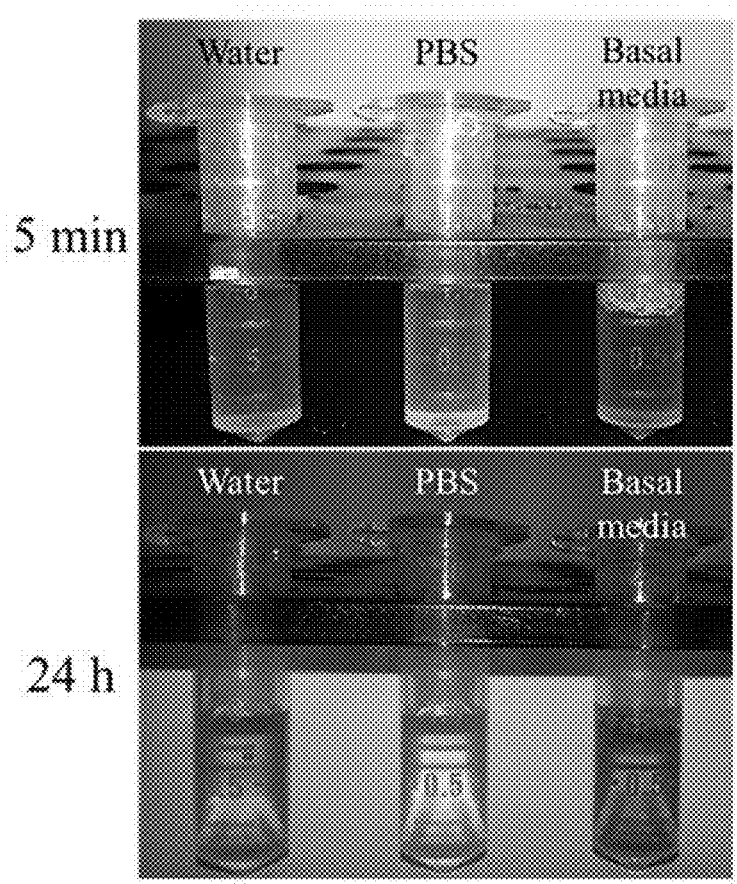
FIGS. 11A-11B Stability test of Au@PDA NPs in water, PBS, and basal media (α-MEM+10% FBS).
Figure 11B:
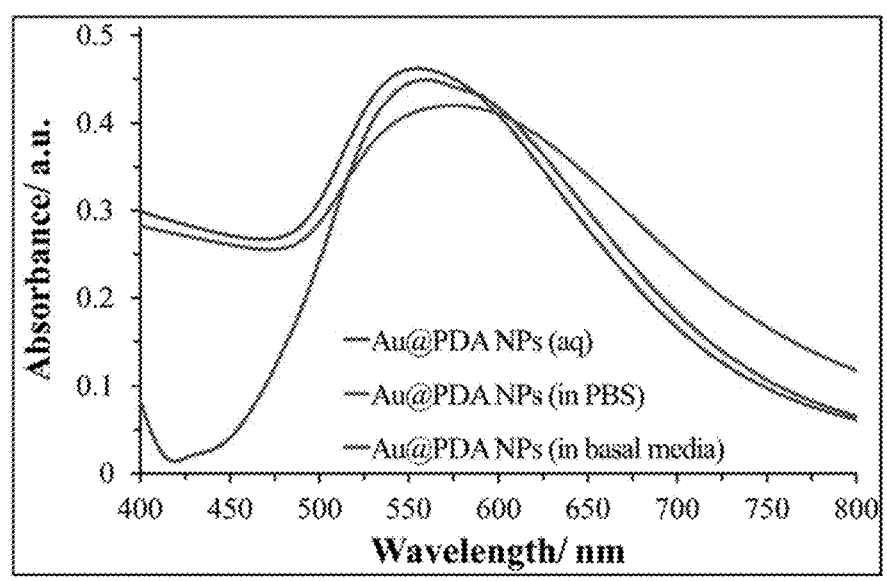
Figure 12:
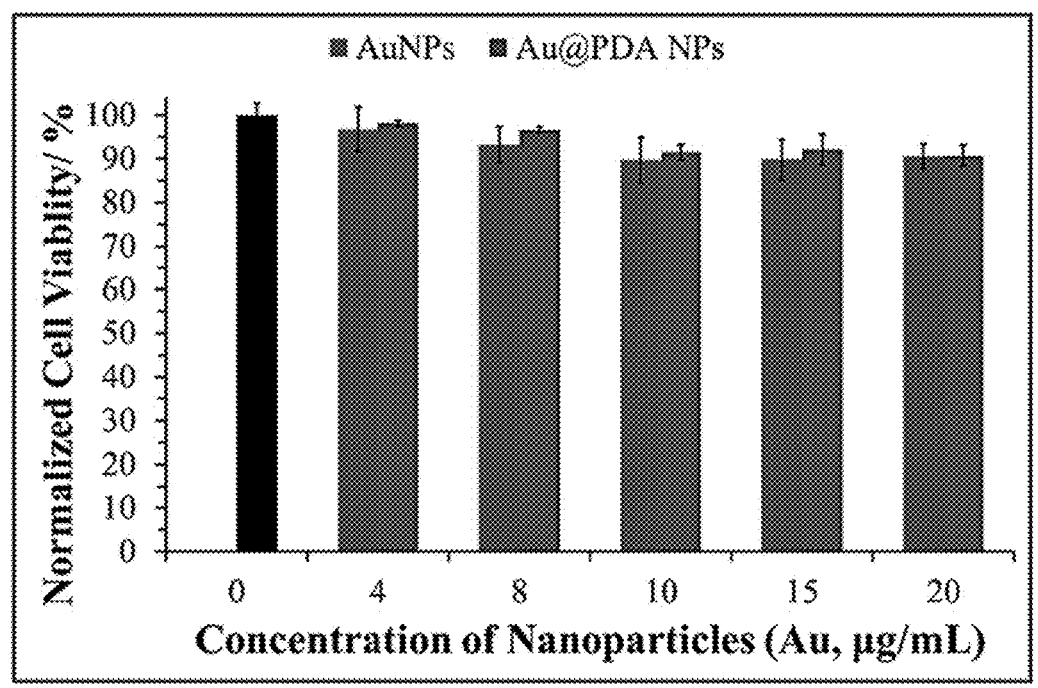
FIG. 12 Cytotoxicity of hMSCs evaluated by the Alamar blue assay after incubation with AuNPs or Au@PDA NPs at different concentrations (expressed as Au content obtained from ICP-OES measurement) for 24 h. Results are normalized using the cytotoxicity data of untreated hMSCs. Data obtained from six independent measurements are presented as mean±SD.

The inventors first prepared citrate-capped AuNPs in a diameter of 42.3±2.7 nm as the core using seed-growth method as previously reported[31]. Inductively coupled plasma optical emission spectrometry (ICP-OES) showed that the atomic Au concentration of the prepared AuNP stock is 40 µg/mL. Caution was taken to maintain the original concentration of the AuNP stock during the subsequent coating process and in all the following experiment. Next, the AuNPs were coated with a uniform and thin PDA shell (4.6±0.3 nm) via in situ polymerization of dopamine, during which AuNPs are ultrasonically dispersed in a solution of dopamine buffered at pH 8.5 for 1 h[32, 33]. A very low concentration of dopamine solution, i.e., 0.05 mg/mL, was used in this study to minimize the self-polymerization of dopamine and to tune the thickness of the PDA shell. As revealed in the UV-vis absorption spectra, coating of PDA on the surface of AuNPs led to a slight red-shift of the maximum peak from 530 nm to 550 nm and an increase in near-infrared (NIR) absorbance (FIG. 2A). The core-shell structure of Au@PDA NPs was clearly visible under transmission electron microscopy (TEM) (FIG. 2B). Typical TEM images showed that Au@PDA NPs possess a physical size of 54.5±4.6 nm (Table 1). Dynamic light scattering (DLS) measurements (FIG. 8) revealed a hydrodynamic diameter of 56.1±1.6 nm for the same batch of Au@PDA NPs (Table 1). Both the TEM and DLS data collectively indicated that the Au@PDA NPs fall within a size range that favors cellular uptake by mammalian cells[34]. It is worth noting that the shell thickness can be easily tuned to the desired range by simply changing the dopamine concentration (FIG. 9). Table 1 summarizes the physiochemical properties of Au@PDA NPs. The difference between the Fourier transform infrared (FT-IR) spectra of the AuNP and Au@PDA NPs further confirms the presence of the PDA shell on the surface of the AuNPs (FIG. 10). Newly emerged absorption bands at 3410 cm$^{-1}$ (stretching vibration of phenolic O—H and N—H), 1605 cm$^{-1}$ (stretching vibration of aromatic ring and bending vibration of N—H), 1510 cm' (shearing vibration of N—H), and 1295 cm$^{-1}$ (stretching vibration of phenolic C—O) all indicated successful coating of PDA on the AuNPs[35]. Afterwards, the colloidal stability of the as-prepared Au@PDA NPs was tested in water, PBS, and basal media for hMSCs. UV-vis spectroscopy shows that the Au@PDA NPs are stable in those solutions for at least 24 h upon the incubation at 37° C. without obvious aggregation (FIG. 11B). Furthermore, the PDA shell showed no significant cytotoxicity[36], as proven by cell viability data collected from hMSCs incubated with different concentrations of nanoparticles for 24 h (FIG. 12).

Preparation and Characterization of Au@PDA-hpDNA Nanoprobes.

It is anticipated that the PDA shell will serve two important design purposes that support the detection of miRNAs inside stem cells. Its abundant catechol and amino groups allow for facile and direct immobilization of DNA strands via π-π interactions and hydrogen bonding [37]. Together with the AuNP core, the PDA shell also assists in quenching the emission of the fluorescently-labeled hairpin DNA (hpDNA) recognition strands to be deposited on its surface [25], resulting in a compounded quenching effect. For the initial studies, FITC-labeled hpDNA strands that specifically recognize miR-29b (sequence information listed in Table 2, denoted hpDNA-29b) were loaded on the surface of Au@PDA NPs by gentle mixing for 1 h to form the Au@PDA-hpDNA (or "nanoprobes") against miR-29b. The fluorescence of free FITC-labeled hpDNAs was then compared with that of nanoprobes immobilized with FITC-hpDNAs. Emission spectra showed that the FITC fluorescence signals of 250 nM of FITC-hpDNAs ($\lambda_{max}$ located at 520 nm) were almost entirely quenched by the Au@PDA NPs (FIG. 2A). These data confirmed the successful adsorption of the FITC-labeled hpDNA strands on the surface of Au@PDA NPs and highlight the excellent fluorescence quenching power of the Au@PDA NPs, most likely due to the combined quenching effect of both the AuNP core and the PDA shell.

Figure 3A:
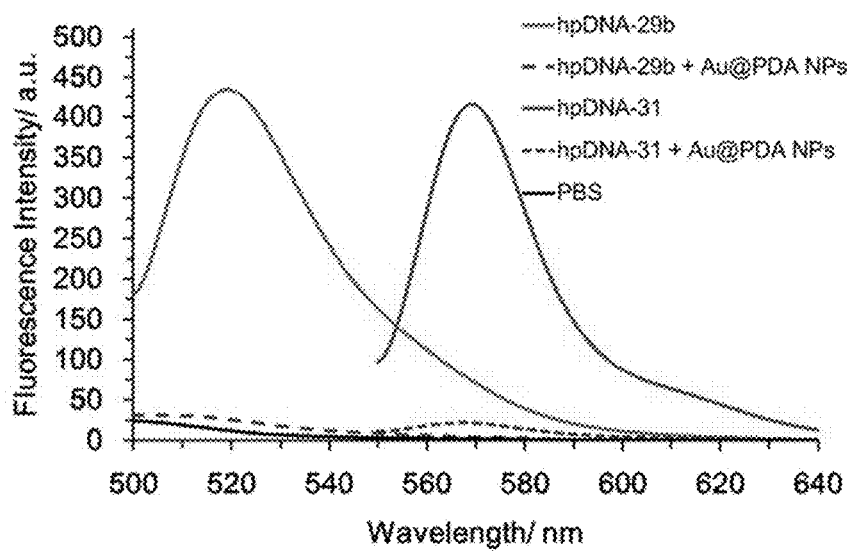
FIGS. 3A-3B FIG. 3A shows Fluorescence emission spectra of 250 nM of dye-labeled hpDNA probes before and after immobilization on the surface of Au@PDA NPs.

To demonstrate the versatility of the Au@PDA NPs, the above quenching experiment was repeated by loading Cy3-labeled hpDNAs that specifically target miR-31 (sequence information listed in Table 2, denoted hpDNA-31), on the surface of Au@PDA NPs. Again, effective quenching of the Cy3 fluorescence ($\lambda_{max}$ located at 565 nm) was observed after 1 h of incubation (FIG. 3A). Taken both the FITC and Cy3 quenching data together, the inventors showed that the quenching is independent of the fluorescent dye attached to and sequence of the hpDNA recognition strands. The robust quenching ability of the Au@PDA NPs may afford a high signal-to-noise ratio in the subsequent intracellular detection of miRNAs.

Figure 3B:
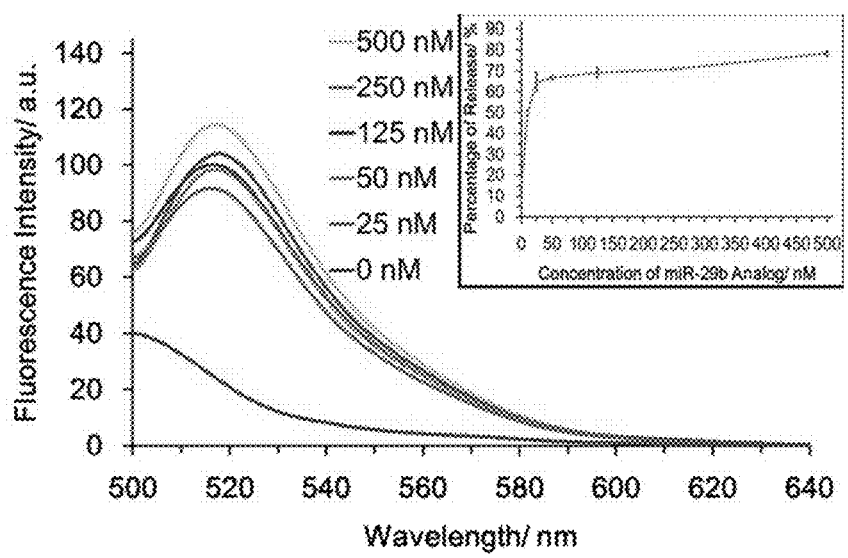
Figure 13:
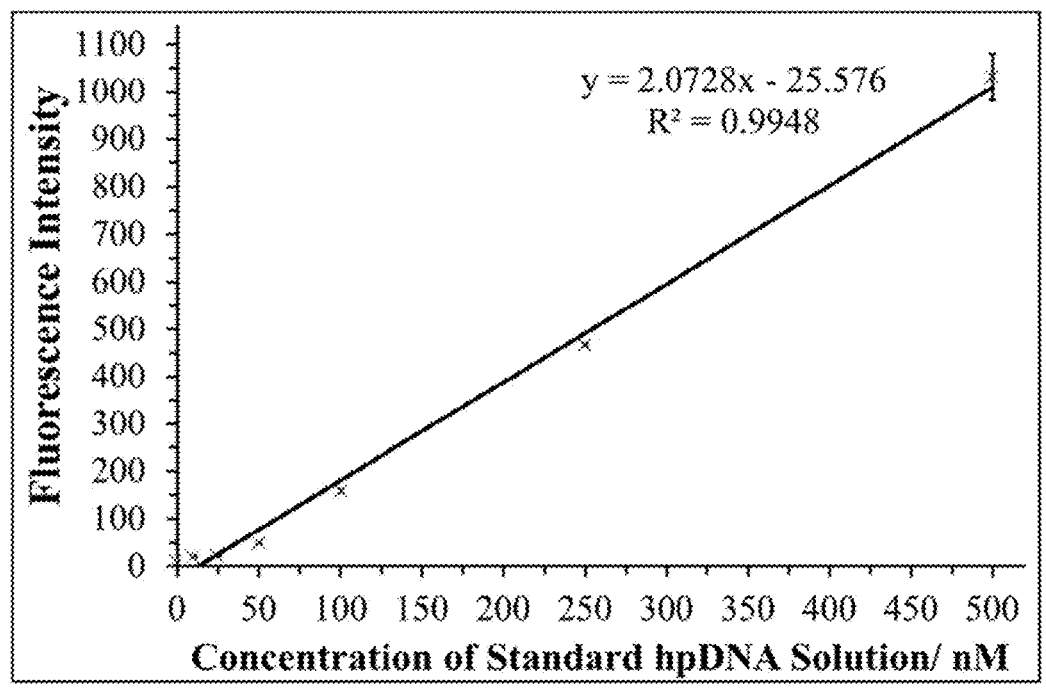
FIG. 13 Standard linear calibration curve used for the estimation of % release of immobilized fluorescently-labeled hpDNA strands onto Au@PDA NPs as shown in the inset of FIG. 2B. Data are recorded from the fluorescence measurements of known concentrations of FITC-labeled hpDNA solutions against miR-29b. Data obtained from three independent measurements are presented as mean±SD.
Figure 14:
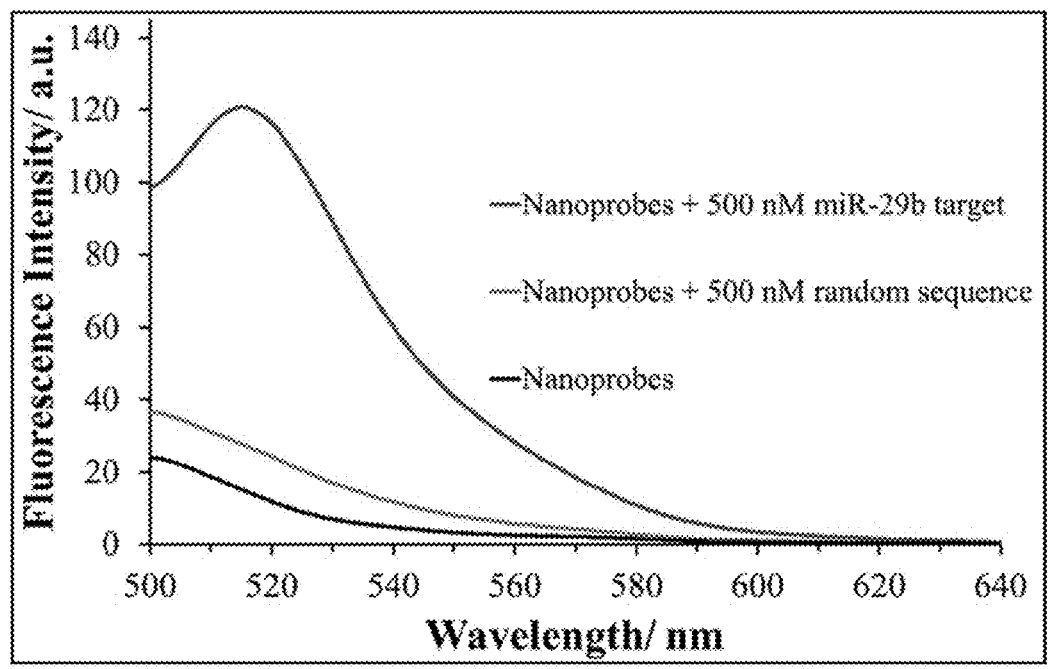
FIG. 14 Release assay of Au@PDA-hpDNA nanoprobes in a buffer system. 100 nM of FITC-labeled hpDNA strands that specifically recognize miR-29b are first immobilized onto Au@PDA NPs to form the nanoprobes against miR-29b. Red trace shows the fluorescence signals of the nanoprobes upon 2 h of incubation with 500 nM of DNA analog of miR-29b (target). Blue trace shows the fluorescence signals of the nanoprobes upon 2 h of incubation with 500 nM of random DNA sequence as control. Purple trace shows the fluorescence signal of the nanoprobes itself. These data support that our nanoprobes show reasonable specificity against miR-29b.

The ability of the nanoprobes to release the immobilized and quenched fluorescent hpDNA strands in the presence of the target miRNA was next assessed. To achieve this, the DNA analog of the target miR-29b (sequence information listed in Table 2) was added to a buffer that contained nanoprobes against miR-29b and any recovery of fluorescence signals due to the specific release of immobilized hpDNAs was subsequently observed. 100 nM of the hpDNA recognition strands against miR-29b were first immobilized onto Au@PDA NPs as aforementioned. Upon 2 h of incubation with the DNA analog of the target miR-29b at a concentration ranging from 25 nM to 500 nM, the FITC emission signals gradually increased with the amount of miR-29b added into the buffer (FIG. 3B). Particularly, in the presence of 250 nM target miR-29b, around 70% of the immobilized FITC-labeled hpDNA strands were released from the Au@PDA NPs (FIG. 3B), as estimated by comparing the recovered fluorescence signals in buffer with a standard curve acquired with known concentrations of the FITC-labeled hpDNA strands (FIG. 13)[38].

Cellular Uptake of Au@PDA NPs.

Figure 4A:
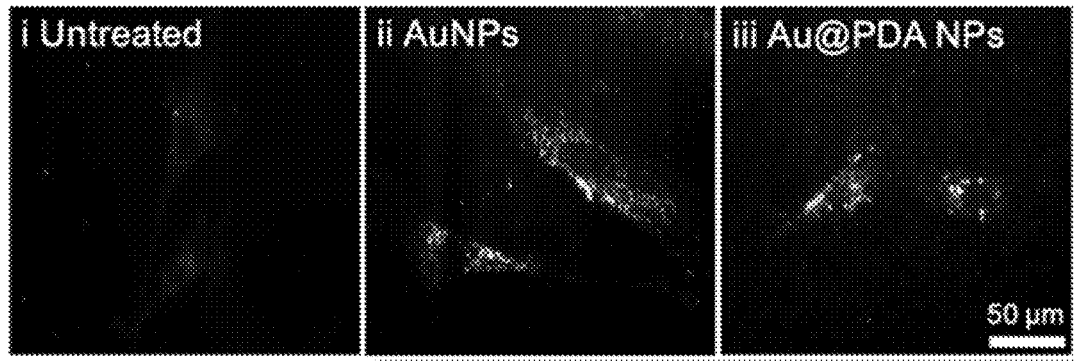
FIGS. 4A-4C Evidence of cellular uptake in hMSCs.
Figure 4B:
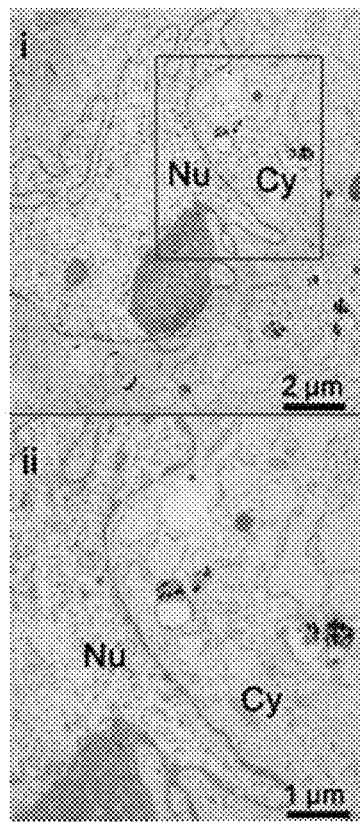
Figure 4C:
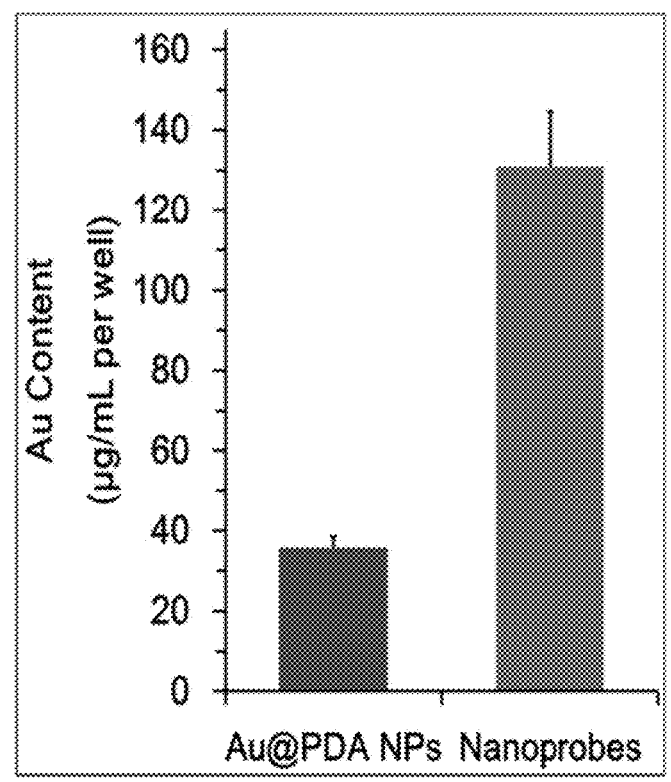
Figure 15:
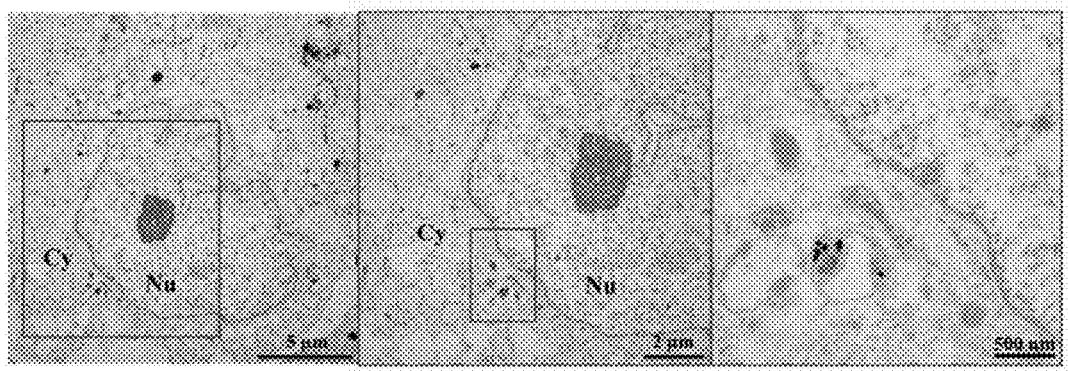
FIG. 15 Representative TEM images of hMSCs incubated with Au@PDA NPs for 24 h. Magnified images show that most uptaken Au@PDA NPs are located in the perinuclear region inside hMSCs. Cy=cytoplasm, Nu=nucleus.
Figure 16:
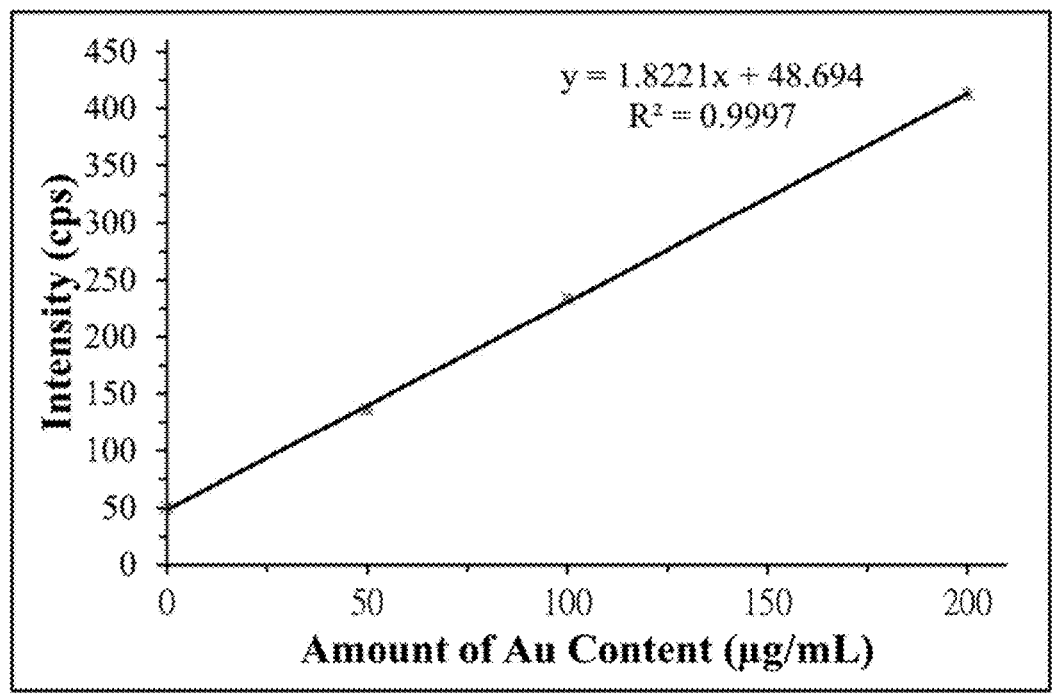
FIG. 16 Standard linear calibration curve obtained from ICP-OES measurements of varying concentration of gold standard solutions. This calibration curve is used to determine the concentration of the stock solution of AuNPs and the Au content per well as shown in FIG. 3C. Error bars represent mean±SD obtained from three independent measurements. Data obtained from three independent measurements are presented as mean±SD.

Despite their negative surface charge of ~39 mV (Table 1), the inventors found that their as-synthesized Au@PDA NPs naturally crossed the cell membrane of hMSCs in abundant amounts without using any cationic[26] or lipophilic transfection agents[39]. This is striking because stem cells, including hMSCs, are indeed difficult to transfect [29]. After cellular entry, most Au@PDA NPs reside in the cytosol or lysosomes as individual particles or clusters, as evidenced in dark-field microscopic and TEM imaging data (FIG. 4A, B). Moreover, most of the uptaken particles were located at the perinuclear region (FIG. 15). Interestingly, ICP-OES data showed that the adsorption of hpDNA strands on the surface of the Au@PDA NPs further increased the cellular uptake of the NPs by 2-3 fold (FIG. 4C). These data indicate that both the PDA shell and the hpDNA oligonucleotides facilitate the uptake of the AuNPs by hMSCs. While the mechanism that governs the uptake of the Au@PDA NPs by stem cells remains unclear at this point, Mirkin and co-workers have demonstrated that attachment of DNA oligonucleotides onto the surface of AuNPs can support the cellular uptake by mammalian cells mediated by class A scavenger receptors and caveolae[40]. In essence, Au@PDA-hpDNA nanoprobes are effective agents for cellular entry, most likely due to the formation of a dense oligonucleotide shell on the surface of Au@PDA NPs by the adsorbed hpDNAs[41].

Intracellular Detection of miRNAs in hMSCs and Monitoring of Differentiation Status.

miR-29b is a well-known positive regulator of osteogenesis robustly expressed in osteoblastic cells [42]. Profiling studies show that the expression of miR-29b in preosteoblasts follows a temporal pattern in which the miR-29b level elevates with the time of osteoblast maturation[42, 43]. A similar trend of miR-29b expression can be observed in stem cells throughout osteogenic differentiation[18, 22]. More recently, miR-31 has been found as another regulator of osteogenesis in hMSCs, which is significantly up-regulated in differentiating hMSCs but not in undifferentiated hMSCs [21]. The dynamic nature in intracellular levels of such specific miRNAs governed by the osteogenic differentiation inspires us to investigate whether intracellular tracking of miR-29b and miR-31 can assist in the monitoring of the osteogenesis progress of stem cells or identification of osteoblastic cells.

Figure 5A:
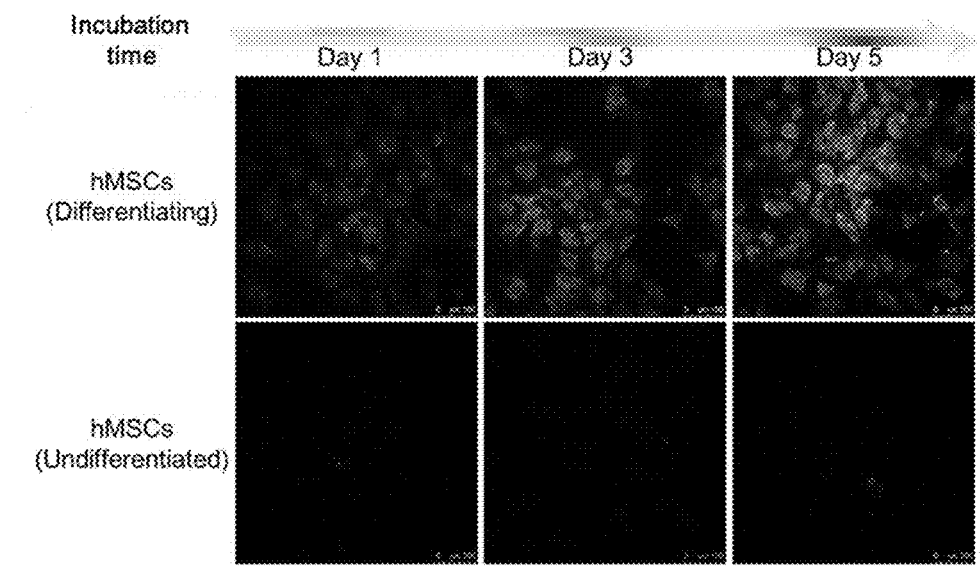
FIGS. 5A-5B Monitoring of differentiation progress of hMSCs via the intracellular detection of miRNAs.

To test the hypothesis, 10 μg/mL of nanoprobes carrying immobilized FITC-labeled hpDNAs that specifically recognize miR-29b were incubated with hMSCs in basal media (containing no osteogenesis-inducing factors). After 24 h of cellular uptake, hMSCs were thoroughly rinsed and cultured either in basal media as control or in osteogenic induction media[5] in which hMSCs will progressively differentiate into osteoblasts. Confocal laser scanning microscopic (CLSM) images of the treated hMSCs were taken at different time points after the uptake of the nanoprobes. Representative confocal images show weak but observable fluorescence signals (green channel) in the treated hMSCs after 1 day of osteogenic culture (FIG. 5A), indicating that the nanoprobes are capable of detecting miRNA targets at low initial concentrations. The fluorescence signals in the differentiating hMSCs increasec significantly over time and became very intense on day 5 (FIG. 5A). These gradual and yet drastic changes in intracellular fluorescence with osteo-induction time indeed matched well with the increasing trend of miRNA expression observed in previous profiling studies [18,22]. Apparently, not all the differentiating hMSCs exhibit the same level of fluorescence. This is probably due to the inherent variation in the differentiation potential among the hMSC population, which is known to be phenotypically heterogeneous[44, 25]. As a negative control experiment, the undifferentiated hMSCs cultured in basal media do not show any significant FITC fluorescence over the same observation time window (FIG. 5A). The sharp difference in the fluorescence responses between the differentiating and undifferentiated hMSCs reveals the specificity and sensitivity of the Au@PDA-hpRNA nanoprobes in detecting miR-29b in living stem cells.

Figure 5B:
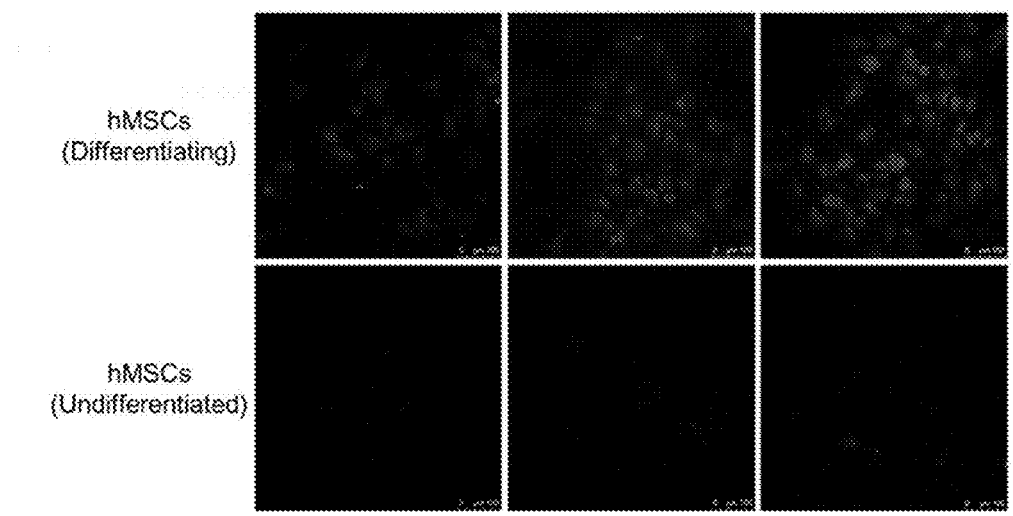

To demonstrate the versatility of the nanoprobes, the inventors repeated the detection assay in hMSCs using nanoprobes containing Cy3-labeled hpDNA strands to detect miR-31. Again, they observed increasing Cy3 fluorescence responses (red channel) over time only in the hMSCs cultured in osteogenic induction media but not the hMSCs cultured in basal media (FIG. 5B).

For both the FITC and Cy3 probes, the target-triggered fluorescence signals from the nanoprobes persisted inside the differentiating hMSCs up to 5 days after the initial cellular entry. Taken together, the results proved the stability of the nanoprobes and their capability of monitoring the differentiation progress of hMSCs. This is believed to be the first study that reports the long-term tracking of miRNA expressions in living stem cells.

Figure 6:
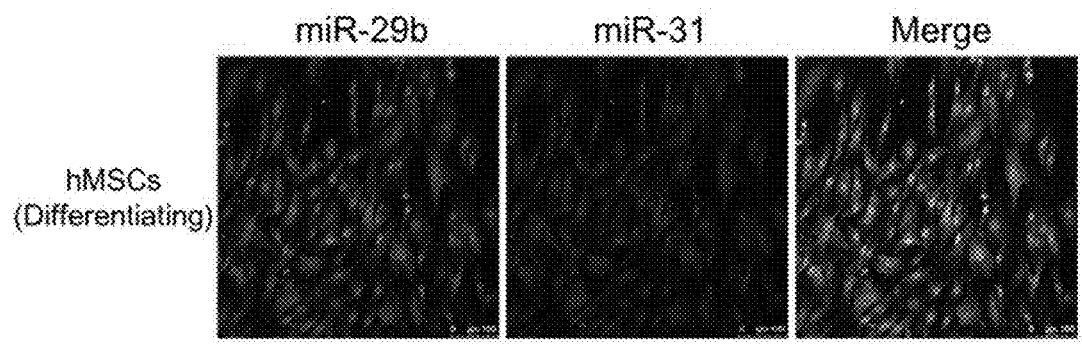
FIG. 6 Multiplexed detection of miRNAs in hMSCs. Confocal images of nanoprobe-treated hMSCs grown in osteogenic induction media for 3 days. Nuclei are counterstained by DAPI. Scale bar is 100 µm. Results show that hMSCs cultured in osteogenic induction media for 3 days express both miR-29b and miR-31.

For enhanced monitoring of the differentiation process of stem cells, simultaneous detection of multiple miRNA targets in living stem cells is desired. The inventors prepared multiplexed Au@PDA-hpDNA nanoprobes for detecting both miR-29b and miR-31 in hMSCs simultaneously. To achieve this, both FITC-labeled hpDNAs against miR-29b (green channel) and Cy3-labeled hpDNAs against miR-31 (red channel) were immobilized on the surface of Au@PDA NPs to form the multiplexed nanoprobes. By incubating these multiplexed nanoprobes with the differentiating hMSCs, both green and red fluorescence signals were observed in the treated hMSCs after 3 days of osteogenic induction (FIG. 6), indicating co-expression of miR-29 and miR-31 in differentiating hMSCs. As the concentration of each dye-labeled hpDNA probe was halved in the preparation of the multiplexed nanoprobes, weaker fluorescence signals were observed compared with images shown previously in FIG. 4. Further studies will be devoted to optimizing the loading efficiency of multiple hpDNAs onto the Au@PDA NPs by either varying the size of the gold nanoparticle core or the thickness of the PDA shell, in order to tune the surface area and affinity of Au@PDA NPs for efficient immobilization of the hpDNAs.

Intracellular Detection of miRNAs in Primary Osteoblasts and 3T3 Fibroblasts.

Figure 7A:
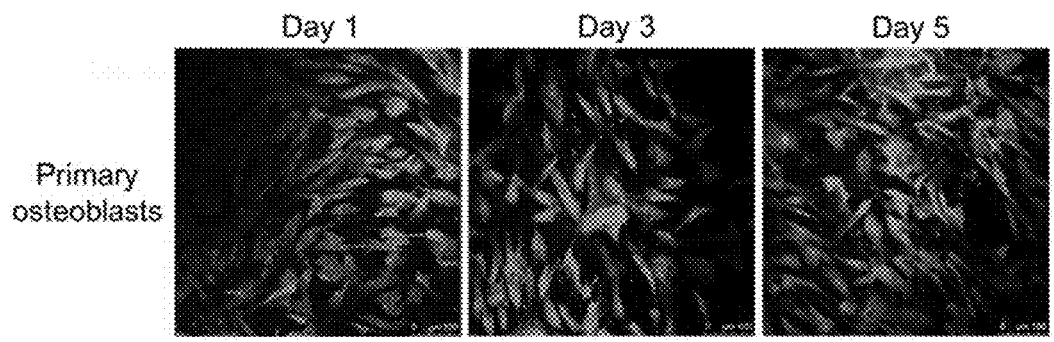
FIGS. 7A-7B Intracellular detection of miR-29b in FIG. 7A shows primary osteoblasts and FIG. 7B shows 3T3 fibroblasts. Representative confocal images show that osteoblasts highly express miR-29b while 3T3 fibroblasts show negligible responses with the nanoprobes targeting miR-29b. Corresponding bright-field images of 3T3 fibroblasts are shown in the bottom panel for reference. Scale bar is 100 µm.
Figure 7B:
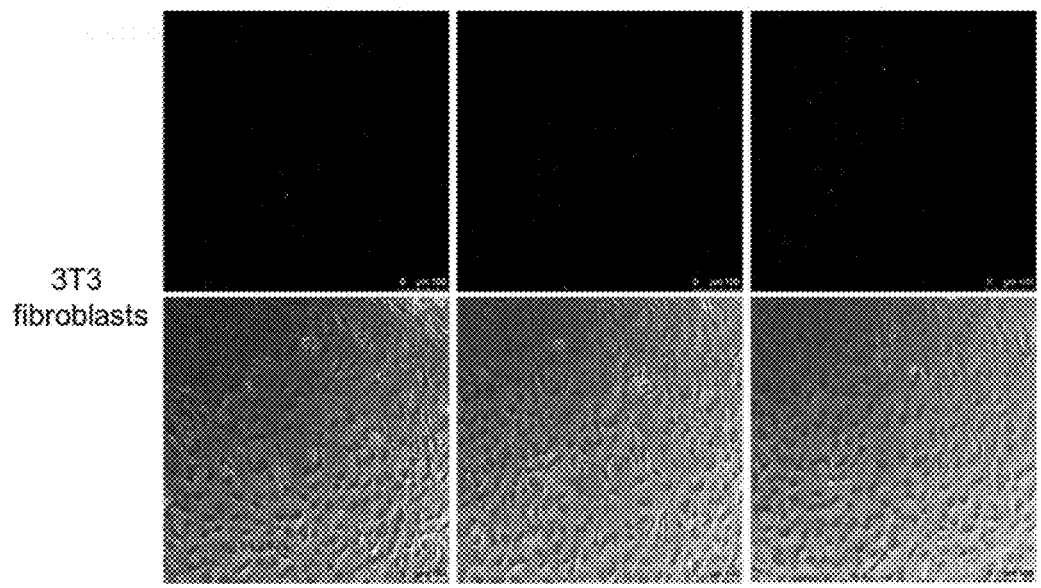
Figure 17A:
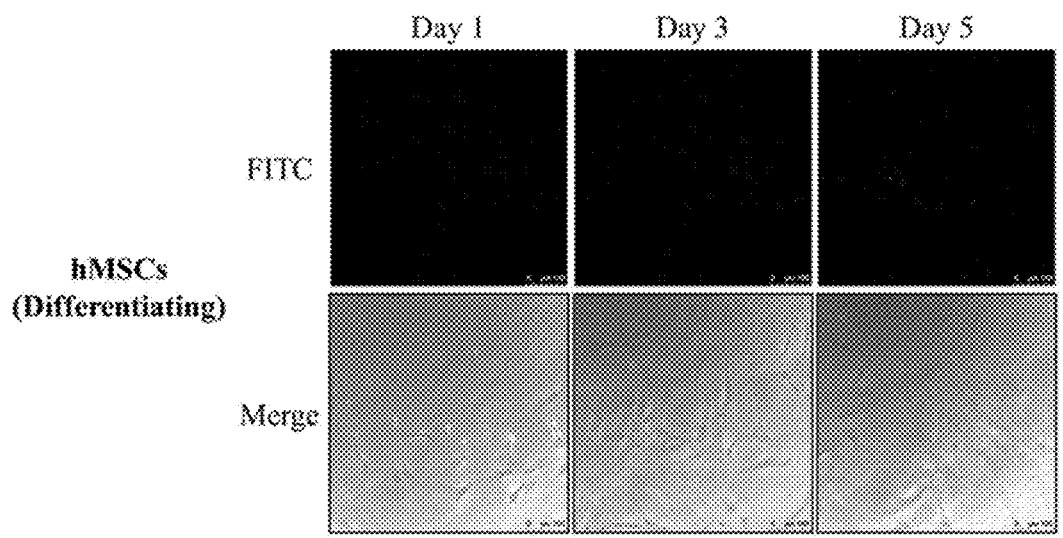
FIGS. 17A-17B Intracellular specificity and stability of Au@PDA-hpDNA nanoprobes. 500 nM of the FITC-labeled scrambled DNA strands are immobilized onto Au@PDA NPs and then incubated with FIG. 17A hMSCs and FIG. 17B primary osteoblasts for 24 h. Cells are imaged at the selected time points after incubation. Results show negligible fluorescence responses in both differentiating hMSCs and osteoblasts, indicating that our nanoprobes are specific and resistant to nuclease degradation for at least 5 days of culture. Nuclei were counter-stained with DAPI. Scale bar is 100 μm. DAPI=4,6-diamidino-2-phenylindole.
Figure 17B:
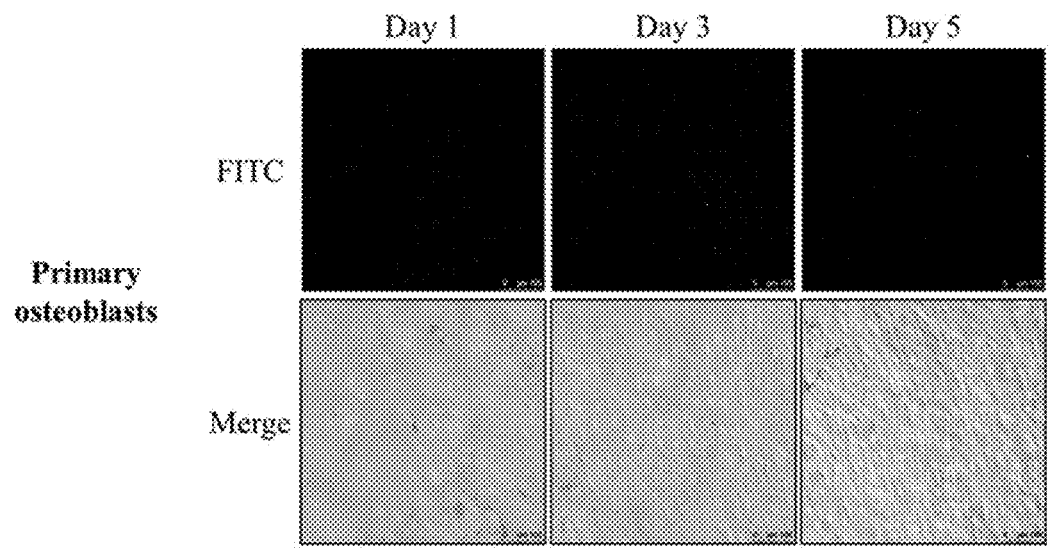
Figure 18:
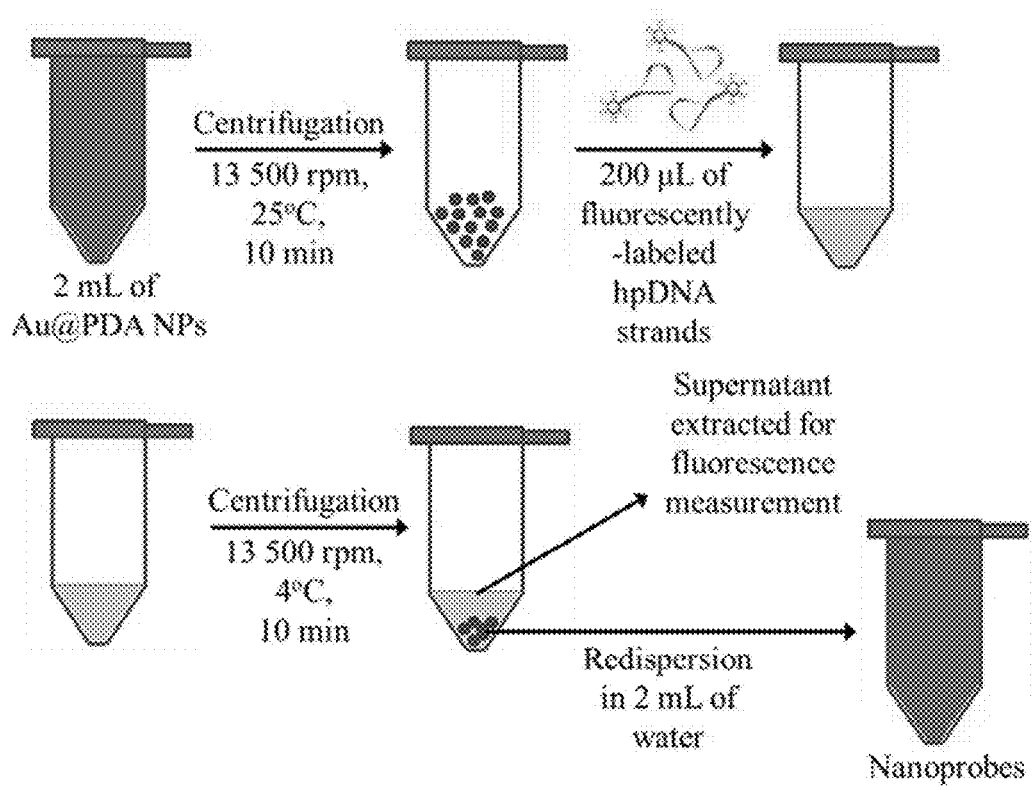
FIG. 18 Monitoring of the immobilization of fluorescently-labeled hpDNA strands on the surface of Au@PDA NPs. All nanoprobes used in this study are prepared in the same manner as described.

To further evaluate the ability of the Au@PDA-hpDNA nanoprobes to detect miRNAs in other cell types, the same procedures for detecting miR-29b were repeated using primary osteoblasts and 3T3 fibroblasts. Osteoblasts, which constitutively express high levels of miR-29b during growth [42, 43], were used here as the positive control for the differentiating hMSCs. Meanwhile, 3T3 fibroblasts, which express minimal level of miR-29b[46], were chosen as the negative control. Osteoblasts and 3T3 fibroblasts were treated identically as hMSCs with the nanoprobes against miR-29b before confocal imaging. As expected, osteoblasts exhibited the highest level of fluorescence signals among the three tested cell types after 5 days of culture (FIG. 7A). Interestingly, a nearly constant level of fluorescence was observed in the osteoblasts from day 1 to day 5 of culture. In sharp contrast, 3T3 fibroblasts showed negligible fluorescence signals after the same period of culture (FIG. 7B). To confirm that the bright signals observed in the osteoblasts and differentiating hMSCs did not stem from intracellular degradation by nucleases, Au@PDA-hpDNA nanoprobes carrying a FITC-labeled scrambled hpDNA sequence (sequence information listed in Table 2) were incubated with the same cell types as a negative control study. Confocal images showed no obvious fluorescence response in both osteoblasts and differentiating hMSCs even after 5 days of culture (FIG. 17). Taken together, these results demonstrate that the Au@PDA-hpDNA nanoprobes are capable of elucidating the relative expression of specific miRNA target(s) in various types of mammalian cells.

Conclusions

In this disclosure it is reported that the sequence-specific detection of two osteogenic miRNA markers, miR-29b and miR-31, in living stem cells using the cell-penetrating Au@PDA-hpDNA nanoprobes described herein. More significantly, the inventors have not only established an approach to distinguishing differentiating from undifferentiated stem cells, but also demonstrated time-dependent and dynamic expression of specific miRNAs in differentiating stem cells. The capability of their nanoprobes for multiplexed detection of miRNAs allows enhanced monitoring of cellular events (e.g., differentiation) in living stem cells. In addition, the specificity of the nanoprobes of this invention enables the identification of osteoblastic cells such as primary osteoblasts from the non-osteoblastic cells such as 3T3 fibroblasts. Furthermore, the modular design of such nanoprobes offers facile switching of customized hairpin DNA probes (including the type of fluorescent labels and sequence), thus opening up the avenue for detecting other biomarkers such as mRNAs in living stem cells. It is believed that the Au@PDA-hpDNA nanoprobes of this invention have great utilities in the investigation on the dynamics of stem cell differentiation, identification and isolation of specific cell types, and high-throughput drug screening.

Experimental Procedure

Synthesis of AuNP@PDA NPs.

All chemicals used in this study were ordered from Sigma Adrich unless otherwise specified. Citrate-stabilized AuNPs of ~40 nm in diameter were synthesized according to the previously reported method with minor modifications.[31] The concentration of AuNPs was determined by an Optima 4300DV inductively coupled plasma optical emission spectrometer (PerkinElmer). Freshly prepared AuNPs were coated with a PDA shell. To decorate the gold core with a PDA shell of ~5 nm in thickness, 10 mL of the AuNP stock solution (Au content as 40 µg/mL) was mixed with 10 mL of the dopamine solution (0.1 mg/mL, buffered in 10 mM Tris at pH 8.5) under continuous sonication at 20 kHz (Banson) for 1 h at room temperature. The purification of the as-prepared Au@PDA NPs was achieved by repeated centrifugation (Hettich) at 14 000 rpm for 10 min. The purified Au@PDA NPs were re-dispersed in Nanopure water (Thermo Scientific).

Characterization of Au@PDA NPs.

UV-vis absorption spectra of the AuNP and Au@PDA NP solutions were recorded with a Cary 5000 UV-vis spectrophotometer (Agilent). The functional groups of the AuNP before and after PDA coating were analyzed with a Nicolet iS10 Fourier transform infrared spectrometer (Thermo Scientific). The nanoparticles were imaged by a Techni TS12 electron microscope (FEI) using a beam voltage of 120 kV. Over 100 particles were selected in multiple images from different areas of the copper grid (Electron Microscopy Sciences) and measured to determine the physical size using ImageJ (NIH). Hydrodynamic size and zeta potential were determined by a ZetaPlus zeta potential analyzer (Brookhaven Instruments).

Synthesis of Au@PDA-hpDNA Nanoprobes.

All oligonucleotides used for this study were purchased (TaKaRa) and used without further purification. In a typical synthesis, Au@PDA-hpDNA nanoprobes (including nanoprobes that contain a scrambled DNA sequence) were prepared via the immobilization of fluorescently-labeled hpDNAs on the surface of Au@PDA NPs. To achieve this, 2 mL of 40 µg/mL of Au@PDA NP solution was concentrated 10 times by centrifugation. 200 µL of 500 nM the DNA solution (prepared in PBS) was then added to disperse the pellet and the mixture was allowed to incubate at room temperature for 1 h. Excess DNA strands were removed by centrifugation (Eppendorf). The pellet was re-dispersed in water to restore the initial concentration of the AuNP stock. For the multiplexed nanoprobes, 100 µL of FITC-labeled hpDNAs against miR-29b (500 nM) and Cy3-labeled hpDNAs against miR-31 (500 nM) were mixed first before incubating with Au@PDA NPs.

Quenching and Release Assay of Nanoprobes.

To monitor the immobilization of hpDNA probes on the surface of Au@PDA NPs, fluorescence measurements were carried out using a fluorescence spectrophotometer (Hitachi). The experimental procedures were graphically illustrated in FIG. 8. Briefly, the mixture of hpDNAs and Au@PDA NPs after 1 h of incubation was spun down and the supernatant was extracted for further investigation. The fluorescence signal of the free hpDNA solution was recorded as the reference. DNA analog of miR-29b (i.e., the complementary DNA sequence of the recognition region of the hpDNA probe against miR-29b) was used as the target for the extracellular studies. Subsequently, the nanoprobes carrying immobilized FITC-labeled hpDNA-29b (100 nM) were mixed with different concentrations of target (0, 10, 25, 50, 125, 250, and 500 nM) and allowed to hybridize for 2 h. The mixture was then centrifuged and the supernatant was extracted to obtain the release profile. The recorded fluorescence intensity was compared with the reference intensity. A random DNA sequence was used to test the specificity of the nanoprobes against miR-29b in buffer.

Cell Culture.

All cell experiments associated in this study involve the culturing of cells at 37° C. and 5% $CO_2$. hMSCs (Lonza) were expanded to passage 3 in basal media (α-MEM supplemented with 10% FBS, 1% streptomycin/penicillin, and 1% L-glutamine; Invitrogen). To induce osteogenesis, HMSCs were cultured in induction media (basal media added with 10 mM bone morphogenetic protein, 50 µg/mL L-ascorbic acid 2-phosphate, and 100 nM dexamethasone). Primary mouse osteoblasts were a gift from Professor Gang Li in The Chinese University of Hong Kong. Osteoblasts were grown and expanded to passage 3 in DMEM supplied with 10% FBS, 1% streptomycin/penicillin, and 1% L-glycine. 3T3 mouse fibroblasts were expanded in basal media.

Cell Viability.

hMSCs were seeded at a density of 5000 cells/cm² and grown to ~80% confluence. Cells were then incubated with nanoparticles at varying concentrations (4-20 µg/mL) for 24 h. The viability of the cells was estimated by the Alamar blue assay (Invitrogen). All experiments were carried out in triplicate. The nanoparticle-associated cytotoxicity was represented as the absorbance at 570 nm normalized by the data from untreated hMSCs.

Dark-Field Microscopy.

Cellular uptake of the nanoparticles by hMSCs was qualitatively examined by dark-field microscopy using an inverted IX70 microscope equipped with an illumination condenser (Olympus). Cells were grown on 35 mm coverglass bottom dish (SPL Lifescience) and treated with 10 µg/mL of nanoparticles (both AuNPs and Au@PDA NPs) for 24 h. Cells were thoroughly rinsed with DPBS (Invitrogen) before imaging.

TEM.

hMSCs were grown in a 6-well plate (SPL Lifescience) and incubated with 10 µg/mL of Au@PDA NPs for 24 h. The treated cells were then trypsinized and centrifuged. The cell pellets were fixed in 4% paraformaldehyde (PFA) in PBS for 15 min. Cells were then centrifuged again and the pellets were enrobed in molten 2% agarose at 37° C. The mixture was then gelated in water at room temperature. Afterwards, the cell-containing gels were fixed in 2.5% glutaraldehyde in 100 mM sodium cacodylate buffer (pH=7.4), stained by 1% OsO4 and by 0.9% $OsO_4$ and 0.3% $K_4Fe(CN)_6$, with all steps carried out at 4° C. for 2 h. The treated gels were gradually dehydrated with ethanol and propylene oxide. Following that, the cell-containing gels were embedded in Epon 812 resins (Electron Microscopy Sciences) and further polymerized. The sectioned samples (80 nm) were finally deposited on 200-mesh copper grids (Electron Microscopy Sciences) and stained with 2% uranyl acetate (SPI Supplies) and Reynolds lead citrate. TEM images were recorded under a H7700 Transmission Electron Microscope (Hitachi) using a beam voltage of 80 kV.

ICP-OES.

hMSCs were grown in a 24-well plate (SPL Lifescience) and incubated with 10 µg/mL of AuNPs or Au@PDA NPs for 24 h. Following that, the treated cells were thoroughly rinsed. Cell pellets were obtained and then digested in 0.25 mL of freshly prepared aqua regia ($HCl:HNO_3$=1:3, v/v) at 55° C. for 30 min. After adding 0.08 mL of 1000 ppm indium (internal standard; AccuStandard) and 3.52 mL of matrix solution (2% HCl and 2% $HNO_3$), the atomic Au content in the resultant solution was determined by ICP-OES. The data obtained from untreated hMSCs were used for background correction.

Confocal Microscopy.

For all of the tested cell types, cells were seeded on coverglass bottom dish and allowed to grow to 80% confluence. Following that, cells were treated with 10 µg/mL of nanoprobes for 24 h. Then, the media containing nanoprobes were aspirated and the cells were washed with DPBS (Invitrogen) thrice. Fresh media was added and the cells were allowed to either grow or differentiate (for hMSCs). At each selected time point (i.e., day 1, day 3, and day 5 after incubation), cells were imaged under a TCS SP5 confocal scanning microscope (Leica). The excitation wavelengths for FITC and Cy3 are 488 nm and 520 nm, respectively. Settings of the microscope were kept constant for all experiments.

Statistical Analysis.

Unless otherwise mentioned, all data are presented as mean±standard deviation. Statistical analysis was performed using two-way ANOVA.

TABLE 1

Physiochemical Properties of AuNPs and Au@PDA NPs.

| Sample | Core size [nm][a] | Shell thickness [nm][a] | Physical size [nm][a] | Hydrodynamic size [nm] (PDI)[b] | Zeta potential [mV][b] |
|---|---|---|---|---|---|
| AuNPs | N.A.[c] | N.A.[c] | 42.3 ± 2.7 | 44.6 ± 0.6 (0.25) | −31.9 ± 2.1 |
| Au@PDA NPs | 43.9 ± 3.4 | 4.6 ± 0.3 | 54.5 ± 4.6 | 56.1 ± 1.6 (0.19) | −39.0 ± 1.5 |

[a]The values are obtained from the analysis of over 100 particles in multiple TEM images by ImageJ.
[b]Measured by Zeta Plus zeta potential analyzer. Results are given in mean ± SD (PDA = poly-dispersity index) of 10 measurements.
[c]Measurement is not applicable to the sample.

TABLE 2

| Name | Sequence |
|---|---|
| hsa-miR-29b | 5'-UAG CAC CAU UUG AAA UCA GUG UU-3' (SEQ ID NO: 1) |
| hsa-miR-31 | 5'-AGG CAA GAU GCU GGC AUA GCU-3' (SEQ ID NO: 2) |
| DNA analog of hsa-miR-29b | 5'-TAG CAC CAT TTG AAA TCA GTG TT-3' (SEQ ID NO: 3) |
| FITC-labeled hpDNA-29b | 5'-FITC-<u>CCG GGT</u> AAC ACT GAT TTC AAA TGG TGC TA <u>ACC CGG</u>-3' (SEQ ID NO: 4) |
| Cy3-labeled hpDNA-31 | 5'-Cy3-<u>CCG GGT</u> AGC TAT GCC AGC ATC TTG CCT <u>ACC CGG</u>-3' (SEQ ID NO: 5) |
| Scrambled FITC-labeled DNA | 5'-FITC-GCT GCT TTA TAG AGC CTG TTG A-3' (SEQ ID NO: 6) |

TABLE 2-continued

| Name | Sequence |
|---|---|
| Random DNA | 5'-CAG TGG TTT TAC CCT ATG GTA G-3' (SEQ ID NO: 7) |

Table 2: DNA sequences employed for the extra- and intracellular detection of miRNAs. All nanoprobes are prepared by immobilizing the hpDNA strands on the surface of Au@PDA NPs upon 1 h of incubation. Scrambled DNA sequence refers to a DNA sequence with the following properties: i) bears the same nucleotide composition as the probe sequence, ii) has no complex sequence, and iii) shows the weakest (or no) matches with any mRNA in the mRNA pool for human. Base pairs in the stem region of the hpDNA probes are underlined for clarity.
Cy3 = cyanine 3,
FITC = fluorescein isothiocyanate.

All patents, patent applications, and other publications, including GenBank Accession Numbers, cited in this application are incorporated by reference in the entirety for all purposes.

REFERENCES (1) Pittenger, M. F.; Mackay, A. M.; Beck, S. C.; Jaiswal, R. K.; Douglas, R.; Mosca, J. D.; Moorman, M. A.; Simonetti, D. W.; Craig, S.; Marshak, D. R. *Science* 1999, 284, 143.
(2) Abdallah, B. M.; Kassem, M. *Gene therapy* 2008, 15, 109.
(3) Caplan, A. I. *Journal of cellular physiology* 2007, 213, 341.
(4) Granchi, D.; Ochoa, G.; Leonardi, E.; Devescovi, V.; Baglio, S. R.; Osaba, L.; Baldini, N.; Ciapetti, G. *Tissue engineering. Part C, Methods* 2010, 16, 511.
(5) Grigoriadis, A. E.; Heersche, J. N.; Aubin, J. E. *The Journal of cell biology* 1988, 106, 2139.
(6) Fukuda, H.; Takahashi, J.; Watanabe, K.; Hayashi, H.; Morizane, A.; Koyanagi, M.; Sasai, Y.; Hashimoto, N. *Stem cells* 2006, 24, 763.
(7) Pruszak, J.; Sonntag, K. C.; Aung, M. H.; Sanchez-Pernaute, R.; Isacson, O. *Stem cells* 2007, 25, 2257.
(8) Kim, T. H.; Lee, K. B.; Choi, J. W. *Biomaterials* 2013, 34, 8660.
(9) Stefani, G.; Slack, F. J. *Nature reviews. Molecular cell biology* 2008, 9, 219.
(10) Hobert, O. *Science* 2008, 319, 1785.
(11) Huntzinger, E.; Izaurralde, E. *Nature reviews. Genetics* 2011, 12, 99.
(12) Chen, C. Z.; Li, L.; Lodish, H. F.; Bartel, D. P. *Science* 2004, 303, 83.
(13) Mizuno, Y.; Yagi, K.; Tokuzawa, Y.; Kanesaki-Yatsuka, Y.; Suda, T.; Katagiri, T.; Fukuda, T.; Maruyama, M.; Okuda, A.; Amemiya, T.; Kondoh, Y.; Tashiro, H.; Okazaki, Y. *Biochemical and biophysical research communications* 2008, 368, 267.
(14) Ivey, K. N.; Muth, A.; Arnold, J.; King, F. W.; Yeh, R. F.; Fish, J. E.; Hsiao, E. C.; Schwartz, R. J.; Conklin, B. R.; Bernstein, H. S.; Srivastava, D. *Cell stem cell* 2008, 2, 219.
(15) Suh, M. R.; Lee, Y.; Kim, J. Y.; Kim, S. K.; Moon, S. H.; Lee, J. Y.; Cha, K. Y.; Chung, H. M.; Yoon, H. S.; Moon, S. Y.; Kim, V. N.; Kim, K. S. *Developmental biology* 2004, 270, 488.
(16) Houbaviy, H. B.; Murray, M. F.; Sharp, P. A. *Developmental cell* 2003, 5, 351.
(17) Oskowitz, A. Z.; Lu, J.; Penfornis, P.; Ylostalo, J.; McBride, J.; Flemington, E. K.; Prockop, D. J.; Pochampally, R. *Proceedings of the National Academy of Sciences of the United States of America* 2008, 105, 18372.
(18) Gangaraju, V. K.; Lin, H. *Nature reviews. Molecular cell biology* 2009, 10, 116.
(19) Gao, J.; Yang, T.; Han, J.; Yan, K.; Qiu, X.; Zhou, Y.; Fan, Q.; Ma, B. *Journal of cellular biochemistry* 2011, 112, 1844.
(20) Suh, J. S.; Lee, J. Y.; Choi, Y. S.; Chung, C. P.; Park, Y. J. *Biomaterials* 2013, 34, 4347.
(21) Baglio, S. R.; Devescovi, V.; Granchi, D.; Baldini, N. *Gene* 2013, 527, 321.
(22) Kaneto, C. M.; Lima, P. S.; Zanette, D. L.; Prata, K. L.; Pina Neto, J. M.; de Paula, F. J.; Silva, W. A., Jr. *BMC medical genetics* 2014, 15, 45.
(23) Seferos, D. S.; Giljohann, D. A.; Hill, H. D.; Prigodich, A. E.; Mirkin, C. A. *Journal of the American Chemical Society* 2007, 129, 15477.
(24) Prigodich, A. E.; Randeria, P. S.; Briley, W. E.; Kim, N. J.; Daniel, W. L.; Giljohann, D. A.; Mirkin, C. A. *Analytical chemistry* 2012, 84, 2062.
(25) Lin, L. S.; Cong, Z. X.; Cao, J. B.; Ke, K. M.; Peng, Q. L.; Gao, J.; Yang, H. H.; Liu, G.; Chen, X. *ACS nano* 2014, 8, 3876.
(26) Dong, H.; Ding, L.; Yan, F.; Ji, H.; Ju, H. *Biomaterials* 2011, 32, 3875.
(27) Ryoo, S. R.; Lee, J.; Yeo, J.; Na, H. K.; Kim, Y. K.; Jang, H.; Lee, J. H.; Han, S. W.; Lee, Y.; Kim, V. N.; Min, D. H. *ACS nano* 2013, 7, 5882.
(28) Yamano, S.; Dai, J.; Moursi, A. M. *Molecular biotechnology* 2010, 46, 287.
(29) Eguchi, A.; Meade, B. R.; Chang, Y. C.; Fredrickson, C. T.; Willert, K.; Puri, N.; Dowdy, S. F. *Nature biotechnology* 2009, 27, 567.
(30) Dubertret, B.; Calame, M.; Libchaber, A. J. *Nature biotechnology* 2001, 19, 365.
(31) Bastus, N. G.; Comenge, J.; Puntes, V. *Langmuir: the ACS journal of surfaces and colloids* 2011, 27, 11098.
(32) Lee, H.; Dellatore, S. M.; Miller, W. M.; Messersmith, P. B. *Science* 2007, 318, 426.
(33) Black, K. C.; Yi, J.; Rivera, J. G.; Zelasko-Leon, D. C.; Messersmith, P. B. *Nanomedicine* 2013, 8, 17.
(34) Chithrani, B. D.; Ghazani, A. A.; Chan, W. C. *Nano letters* 2006, 6, 662.
(35) Jiang, J.; Zhu, L.; Zhu, L.; Zhu, B.; Xu, Y. *Langmuir: the ACS journal of surfaces and colloids* 2011, 27, 14180.
(36) Liu, X.; Cao, J.; Li, H.; Li, J.; Jin, Q.; Ren, K.; Ji, J. *ACS nano* 2013, 7, 9384.
(37) Ham, H. O.; Liu, Z.; Lau, K. H.; Lee, H.; Messersmith, P. B. *Angewandte Chemie* 2011, 50, 732.
(38) Demers, L. M.; Mirkin, C. A.; Mucic, R. C.; Reynolds, R. A., 3rd; Letsinger, R. L.; Elghanian, R.; Viswanadham, G. *Analytical chemistry* 2000, 72, 5535.
(39) Huang, L.; Li, S. *Nature biotechnology* 1997, 15, 620.

(40) Choi, C. H.; Hao, L.; Narayan, S. P.; Auyeung, E.; Mirkin, C. A. *Proceedings of the National Academy of Sciences of the United States of America* 2013, 110, 7625.

(41) Giljohann, D. A.; Seferos, D. S.; Patel, P. C.; Millstone, J. E.; Rosi, N. L.; Mirkin, C. A. *Nano letters* 2007, 7, 3818.

(42) Li, Z.; Hassan, M. Q.; Jafferji, M.; Aqeilan, R. I.; Garzon, R.; Croce, C. M.; van Wijnen, A. J.; Stein, J. L.; Stein, G. S.; Lian, J. B. *The Journal of biological chemistry* 2009, 284, 15676.

(43) Kapinas, K.; Kessler, C.; Ricks, T.; Gronowicz, G.; Delany, A. M. *The Journal of biological chemistry* 2010, 285, 25221.

(44) Sekiya, I.; Larson, B. L.; Smith, J. R.; Pochampally, R.; Cui, J. G.; Prockop, D. J. *Stem cells* 2002, 20, 530.

(45) Bruder, S. P.; Jaiswal, N.; Haynesworth, S. E. *Journal of cellular biochemistry* 1997, 64, 278.

(46) Jiao, J.; Herl, L. D.; Farese, R. V.; Gao, F. B. *PloS one* 2010, 5, e10551.

---

What is claimed is:

1. A nano-construct comprising:
   (1) a core particle comprising gold and having a diameter of 40-50 nm;
   (2) a polymer coating comprising polydopamine on the surface of the core particle having a thickness of 4 to 5 nm; and
   (3) a polynucleotide non-covalently attached to the polymer coating,
   wherein the polynucleotide comprises a core segment of 15-30 nucleotides in length, a first pairing segment located at the 5' of the core segment, and a second pairing segment located at the 3' of the core segment, wherein the polynucleotide is further attached to a fluorescent molecule fluorescein isothiocyanate (FITC) or cyanine 3 (Cy3), wherein:
   when the core segment is not hybridized to its complementary sequence, the first and second pairing segments hybridize with each other so as to allow the polynucleotide to assume a hair-pin configuration and fluorescence from the fluorescent molecule to be quenched, and
   when the core segment is hybridized to its complementary sequence, the first and second pairing segment separate from each other so as to allow the polynucleotide to assume an open configuration and fluorescence from the fluorescent molecule to be detectable.

2. The nano-construct of claim 1, wherein each of the pairing segments is 5-10 nucleotides in length.

3. The nano-construct of claim 1, wherein the core particle is 40-45 nm in diameter.

4. The nano-construct of claim 1, wherein the polymer coating is 4.6±0.3 nm in thickness.

5. A composition comprising the nano-construct of claim 1 and a cell.

6. The composition of claim 5, comprising two or more nano-constructs of claim 1, each nano-construct comprising a different fluorescent molecule and a different core segment.

7. The composition of claim 5, wherein the cell is a live stem cell.

8. A method for introducing a polynucleotide into a live stem cell, comprising contacting the live stem cell with the nano-construct of claim 1.

9. The method of claim 8, wherein the method further comprises the steps of
   (1) contacting the nano-construct of claim 1 with the live stem cell under conditions permissible for the nano-construct to hybridize with an miRNA having a nucleotide sequence complementary to the core segment; and
   (2) detecting a signal from the fluorescent molecule.

10. The method of claim 9, wherein step (2) is repeated at a later time and the fluorescent signal detected at the later time is compared with the fluorescent signal detected at the first time, wherein an increase or decrease from the fluorescent signal detected at the first time indicates an increase or decrease, respectively, in the miRNA level.

11. The method of claim 8, wherein the miRNA is miR-29b or miR-31.

12. A method for making the nano-construct of claim 1, comprising the steps:
   (1) contacting a core particle comprising gold with a polydopamine solution to permit a polydopamine coating to form on the surface of the core particle, wherein the core particle has a diameter of 40-50 nm and the polydopamine coating has a thickness of 4 to 5 nm; and (2) contacting the coated core particle with a polynucleotide to permit the polynucleotide to become non-covalently attached to the polydopamine coating, wherein the polynucleotide comprises a core segment of 15-30 nucleotides in length, a first pairing segment located at the 5' of the core segment, and a second pairing segment located at the 3' of the core segment, wherein the polynucleotide is further attached to a fluorescent molecule fluorescein isothiocyanate (FITC) or cyanine 3 (Cy3), wherein:

when the core segment is not hybridized to its complementary sequence, the first and second pairing segments hybridize with each other so as to allow the polynucleotide to assume a hair-pin configuration and fluorescence from the fluorescent molecule to be quenched, and when the core segment is hybridized to its complementary sequence, the first and second pairing segment separate from each other so as to allow the polynucleotide to assume an open configuration and fluorescence from the fluorescent molecule to be detectable.

* * * * *